(12) United States Patent
Kim et al.

(10) Patent No.: US 7,396,682 B2
(45) Date of Patent: Jul. 8, 2008

(54) METHOD FOR CELL ADHESION AND WOUND HEALING

(75) Inventors: In-San Kim, Taegu (KR); Jung-Eun Kim, Taegu (KR)

(73) Assignee: Regen Biotech, Inc., Seoul (KR)

( * ) Notice: Subject to any disclaimer, the term of this patent is extended or adjusted under 35 U.S.C. 154(b) by 488 days.

(21) Appl. No.: 10/276,479

(22) PCT Filed: Dec. 8, 2000

(86) PCT No.: PCT/KR00/01428

§ 371 (c)(1),
(2), (4) Date: Jun. 11, 2003

(87) PCT Pub. No.: WO01/87327

PCT Pub. Date: Nov. 22, 2001

(65) Prior Publication Data

US 2004/0052767 A1    Mar. 18, 2004

(30) Foreign Application Priority Data

May 13, 2000    (KR) ............................. 2000-25662

(51) Int. Cl.
*C12N 5/00* (2006.01)
*C07K 2/00* (2006.01)
*C07K 14/00* (2006.01)
*C07K 17/02* (2006.01)
*C07H 21/04* (2006.01)

(52) U.S. Cl. ..................... 435/402; 435/69.1; 530/350; 530/300; 530/402; 536/23.5

(58) Field of Classification Search ................ 536/23.5; 435/69.1, 402; 530/399, 300, 350, 402
See application file for complete search history.

(56) References Cited

U.S. PATENT DOCUMENTS 5,444,164 A    8/1995   Purchio et al. ............. 536/23.5

FOREIGN PATENT DOCUMENTS

WO    WO 96/01102    1/1996

OTHER PUBLICATIONS

Kim, J-E., et al. 2000 Journal of Cellular Biochemistry 77: 169-178.*
Elkins, T., et al. 1990 Journal of Cell Biology 110: 1825-1832.*
LeBaron et al., Journal of Investigative Dermatology, 1995, vol. 104, No. 5, pp. 844-849.
Skonier et al., DNA Cell Biol. 1994, vol. 11, No. 7, pp. 511-522.

* cited by examiner

*Primary Examiner*—Maryam Monshipouri
*Assistant Examiner*—Marsha M Tsay
(74) *Attorney, Agent, or Firm*—JHK Law; Joseph Hyosuk Kim

(57) ABSTRACT

The present invention relates to a method for cell adhesion and wound healing with internal domains of βig-h3. Particularly, the present invention relates to the method of using recombinant proteins comprising one or more of $2^{nd}$ or $4^{th}$ internal domain of βig-h3 for cell adhesion and wound healing, wherein the $2^{nd}$ or $4^{th}$ internal domain of βig-h3 has aspartic acid and isoleucine essential for interaction with integrin which represent a high homology in base sequence of βig-h3 internal domains. The recombinant proteins comprising one or more $2^{nd}$ or $4^{th}$ internal domain of βig-h3 are effective for cell adhesion and wound healing by itself and can be used for developing cell culture medium and wound healing agent.

17 Claims, 23 Drawing Sheets

FIG. 4
A
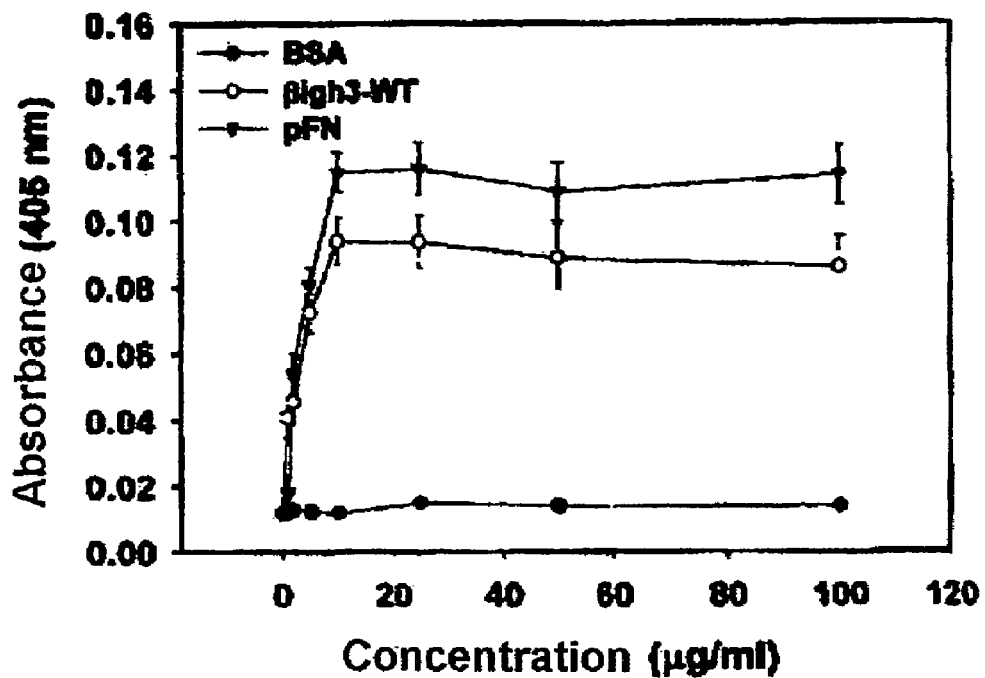
B
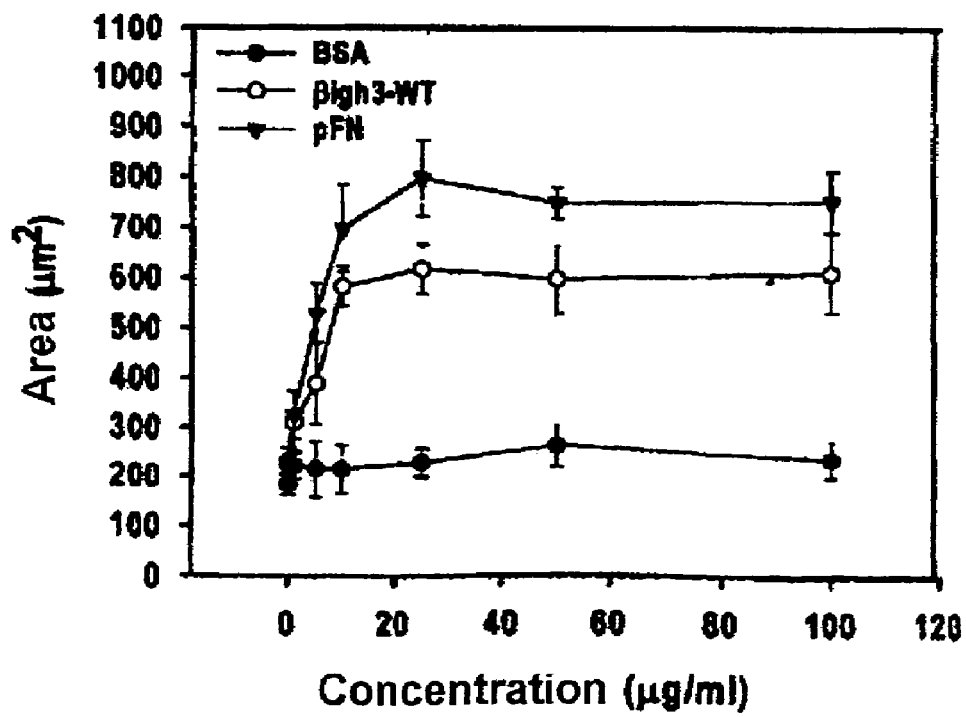

FIG. 5
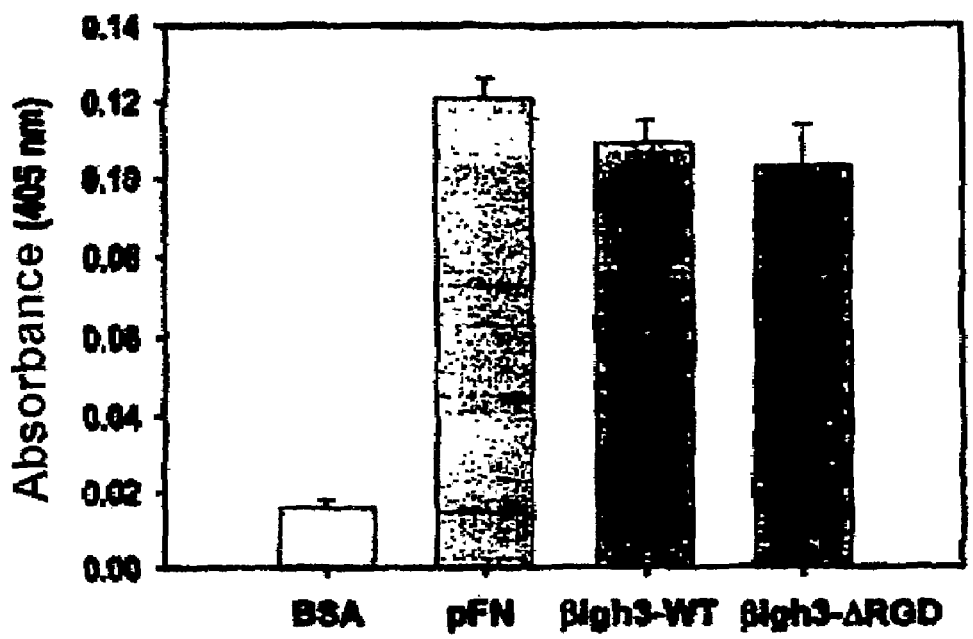
A
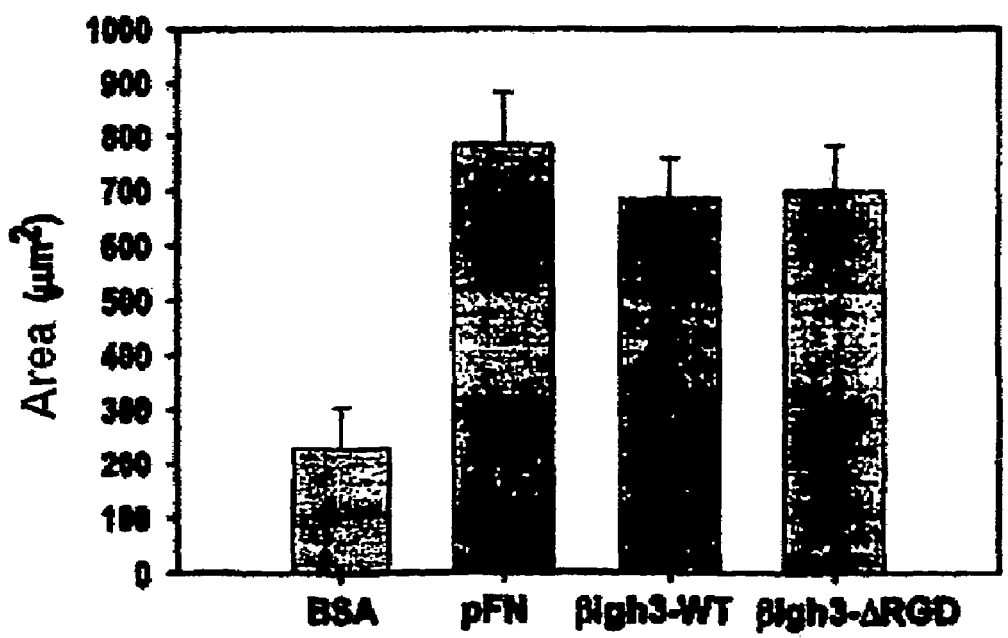
B

FIG. 11

```
                                      H2
BIGH3_HUMAN        211   TVNCARLLKADHHATNGVVHLIDKVI...   236    SEQ ID NO:1
BIGH3_PIG          211   TVNCARLLKADHHATNGVVHLIDKVI...   236    SEQ ID NO:2
BIGH3_CHICK        201   TVNCARLLKADHHATNGVVHVIDKVI...   226    SEQ ID NO:3
BIGH3_HUMAN        346   INGKAIISNKDILATNGVIHYIDELLI..   372    SEQ ID NO:4
BIGH3_PIG          346   INGKPIISNRDVLATNGVIHFIDELLI..   372    SEQ ID NO:5
BIGH3_CHICK        338   INGRAIIANKDILATNGVVHFVNELLI..   364    SEQ ID NO:6
OSF2_HUMAN         340   VNGIKMVNKKDIVTNNGVIHLIDQVLI..   366    SEQ ID NO:7
OSF2_MOUSE         342   INGIKMVNKKDIVTKNGVIHLIDEVLI..   368    SEQ ID NO:8
BIGH3_HUMAN        608   VNKEPVAE-PDIMATNGVVHVITNVL...   632    SEQ ID NO:9
BIGH3_PIG          608   VNKEPVAE-ADIMATNGVVHTINTVL...   632    SEQ ID NO:10
BIGH3_CHICK        600   VNKEPVAE-SDIMATNGVIHAVSSVL...   624    SEQ ID NO:11
SLL1735 homolog    106   VKNATVLA-ADIEADNGIIHVIDNVILMG   133    SEQ ID NO:12
SLL1735            106   VKNATVII-PDIEADNGIIHVIDNVILMG   133    SEQ ID NO:13
SLL1483            152   VHKATVIS-ADVDASNGVIHVIDQVIL..   177    SEQ ID NO:14
OSF2_HUMAN         604   VNELKSKE-SDIMTTNGVIHVVDKLL...   628    SEQ ID NO:15
OSF2_MOUSE         606   VNELKSKE-SDIMTTNGVIHVVDKLL...   630    SEQ ID NO:16
Midline Fasciclin  543   INNLAKIIDAPIMGTNGVLHVIDTIL...   568    SEQ ID NO:17
HLC-32             341   -SKASRVILRDIPTTNGVIQVIDRVIL..   366    SEQ ID NO:18
Midline Fasciclin  825   KIENAGVTRCDVVATNGILHEINDIIV..   851    SEQ ID NO:19
HLC-32             196   TANGARVVEADRKASSGLIHVVDKVI...   221    SEQ ID NO:20 consensus                VNNAARVVKADIHATNGVIHVIDKVLIMG          SEQ ID NO:21
```

FIG. 21
A 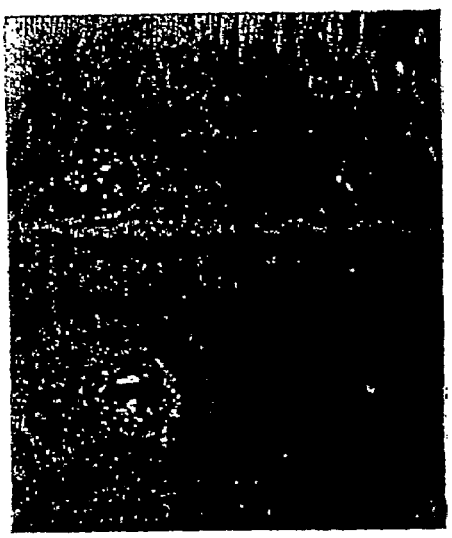 B 
C  D 

US 7,396,682 B2

SEQUENCE LISTING

```
<160> NUMBER OF SEQ ID NOS: 21

<210> SEQ ID NO 1
<211> LENGTH: 26
<212> TYPE: PRT
<213> ORGANISM: HUMAN

<400> SEQUENCE: 1

Thr Val Asn Cys Ala Arg Leu Leu Lys Ala Asp His His Ala Thr Asn
1               5                   10                  15

Gly Val Val His Leu Ile Asp Lys Val Ile
            20                  25

<210> SEQ ID NO 2
<211> LENGTH: 26
<212> TYPE: PRT
<213> ORGANISM: PIG

<400> SEQUENCE: 2

Thr Val Asn Cys Ala Arg Leu Leu Lys Ala Asp His His Ala Thr Asn
1               5                   10                  15

Gly Val Val His Leu Ile Asp Lys Val Ile
            20                  25

<210> SEQ ID NO 3
<211> LENGTH: 26
<212> TYPE: PRT
<213> ORGANISM: CHICKEN

<400> SEQUENCE: 3

Thr Val Asn Cys Ala Arg Leu Leu Lys Ala Asp His His Ala Thr Asn
1               5                   10                  15

Gly Val Val His Val Ile Asp Lys Val Ile
            20                  25
```

<210> SEQ ID NO 4
<211> LENGTH: 27
<212> TYPE: PRT
<213> ORGANISM: HUMAN

<400> SEQUENCE: 4

Ile Asn Gly Lys Ala Ile Ile Ser Asn Lys Asp Ile Leu Ala Thr Asn
1               5                   10                  15

Gly Val Ile His Tyr Ile Asp Glu Leu Leu Ile
            20                  25

<210> SEQ ID NO 5
<211> LENGTH: 27
<212> TYPE: PRT
<213> ORGANISM: PIG

<400> SEQUENCE: 5

Ile Asn Gly Lys Pro Ile Ile Ser Asn Lys Asp Val Leu Ala Thr Asn
1               5                   10                  15

Gly Val Ile His Phe Ile Asp Glu Leu Leu Ile
            20                  25

<210> SEQ ID NO 6
<211> LENGTH: 27
<212> TYPE: PRT
<213> ORGANISM: CHICKEN

<400> SEQUENCE: 6

Leu Asn Gly Arg Ala Ile Ile Ala Asn Lys Asp Ile Leu Ala Thr Asn
1               5                   10                  15

Gly Val Val His Phe Val Asn Glu Leu Leu Ile
            20                  25

<210> SEQ ID NO 7
<211> LENGTH: 27
<212> TYPE: PRT
<213> ORGANISM: HUMAN

<400> SEQUENCE: 7

Val Asn Gly Ile Lys Met Val Asn Lys Lys Asp Ile Val Thr Asn Asn
1               5                   10                  15

Gly Val Ile His Leu Ile Asp Gln Val Leu Ile
            20                  25

<210> SEQ ID NO 8
<211> LENGTH: 27
<212> TYPE: PRT
<213> ORGANISM: MOUSE

<400> SEQUENCE: 8

Ile Asn Gly Ile Lys Met Val Asn Lys Lys Asp Ile Val Thr Lys Asn
1               5                   10                  15

Gly Val Ile His Leu Ile Asp Glu Val Leu Ile
            20                  25

<210> SEQ ID NO 9
<211> LENGTH: 25
<212> TYPE: PRT
<213> ORGANISM: HUMAN

<400> SEQUENCE: 9

```
Val Asn Lys Glu Pro Val Ala Glu Pro Asp Ile Met Ala Thr Asn Gly
1               5                   10                  15

Val Val His Val Ile Thr Asn Val Leu
            20                  25

<210> SEQ ID NO 10
<211> LENGTH: 25
<212> TYPE: PRT
<213> ORGANISM: PIG

<400> SEQUENCE: 10

Val Asn Lys Glu Pro Val Ala Glu Ala Asp Ile Met Ala Thr Asn Gly
1               5                   10                  15

Val Val His Thr Ile Asn Thr Val Leu
            20                  25

<210> SEQ ID NO 11
<211> LENGTH: 25
<212> TYPE: PRT
<213> ORGANISM: CHICKEN

<400> SEQUENCE: 11

Val Asn Lys Glu Pro Val Ala Glu Ser Asp Ile Met Ala Thr Asn Gly
1               5                   10                  15

Val Ile His Ala Val Ser Ser Val Leu
            20                  25

<210> SEQ ID NO 12
<211> LENGTH: 28
<212> TYPE: PRT
<213> ORGANISM: Artificial Sequence
<220> FEATURE:
<223> OTHER INFORMATION: SLL1735 Homolog

<400> SEQUENCE: 12

Val Lys Asn Ala Thr Val Leu Ala Ala Asp Ile Glu Ala Asp Asn Gly
1               5                   10                  15

Ile Ile His Val Ile Asp Asn Val Ile Leu Met Gly
            20                  25

<210> SEQ ID NO 13
<211> LENGTH: 28
<212> TYPE: PRT
<213> ORGANISM: Synechococcus PCC7002

<400> SEQUENCE: 13

Val Lys Asn Ala Thr Val Ile Ile Pro Asp Ile Glu Ala Asp Asn Gly
1               5                   10                  15

Ile Ile His Val Ile Asp Asn Val Ile Leu Met Gly
            20                  25

<210> SEQ ID NO 14
<211> LENGTH: 26
<212> TYPE: PRT
<213> ORGANISM: Synechocystis PCC6803

<400> SEQUENCE: 14

Val Asn Lys Ala Thr Val Ile Ser Ala Asp Val Asp Ala Ser Asn Gly
1               5                   10                  15

Val Ile His Val Ile Asp Gln Val Ile Leu
            20                  25
```

```
<210> SEQ ID NO 15
<211> LENGTH: 25
<212> TYPE: PRT
<213> ORGANISM: HUMAN

<400> SEQUENCE: 15

Val Asn Glu Leu Lys Ser Lys Glu Ser Asp Ile Met Thr Thr Asn Gly
1               5                   10                  15

Val Ile His Val Val Asp Lys Leu Leu
            20                  25

<210> SEQ ID NO 16
<211> LENGTH: 25
<212> TYPE: PRT
<213> ORGANISM: MOUSE

<400> SEQUENCE: 16

Val Asn Glu Leu Lys Ser Lys Glu Ser Asp Ile Met Thr Thr Asn Gly
1               5                   10                  15

Val Ile His Val Val Asp Lys Leu Leu
            20                  25

<210> SEQ ID NO 17
<211> LENGTH: 26
<212> TYPE: PRT
<213> ORGANISM: Drosophila melanogaster

<400> SEQUENCE: 17

Ile Asn Asn Leu Ala Lys Ile Ile Asp Ala Asp Ile Met Gly Thr Asn
1               5                   10                  15

Gly Val Leu His Val Ile Asp Thr Ile Leu
            20                  25

<210> SEQ ID NO 18
<211> LENGTH: 26
<212> TYPE: PRT
<213> ORGANISM: Echinoidea

<400> SEQUENCE: 18

Ser Lys Ala Ser Arg Val Ile Leu Arg Asp Ile Pro Thr Thr Asn Gly
1               5                   10                  15

Val Ile Gln Val Ile Asp Arg Val Ile Leu
            20                  25

<210> SEQ ID NO 19
<211> LENGTH: 27
<212> TYPE: PRT
<213> ORGANISM: Drosophila melanogaster

<400> SEQUENCE: 19

Lys Ile Glu Asn Ala Gly Val Thr Lys Cys Asp Val Val Ala Thr Asn
1               5                   10                  15

Gly Ile Leu His Glu Ile Asn Asp Ile Ile Val
            20                  25

<210> SEQ ID NO 20
<211> LENGTH: 26
<212> TYPE: PRT
<213> ORGANISM: Echinoidea

<400> SEQUENCE: 20

Thr Ala Asn Gly Ala Arg Val Val Glu Ala Asp Arg Lys Ala Ser Ser
1               5                   10                  15
```

```
Gly Leu Ile His Val Val Asp Lys Val Ile
            20                  25

<210> SEQ ID NO 21
<211> LENGTH: 29
<212> TYPE: PRT
<213> ORGANISM: Artificial Sequence
<220> FEATURE:
<223> OTHER INFORMATION: consensus

<400> SEQUENCE: 21

Val Asn Asn Ala Ala Arg Val Val Lys Ala Asp Ile His Ala Thr Asn
1               5                   10                  15

Gly Val Ile His Val Ile Asp Lys Val Leu Ile Met Gly
            20                  25
```

METHOD FOR CELL ADHESION AND WOUND HEALING

CONTINUING DATA

The present application is a U.S. national phase application under 35 U.S.C. §371, of PCT/KR00/01428, filed Dec. 8, 2000.

FIELD OF THE INVENTION

The present invention relates to peptides for use in cell adhesion and wound healing. More particularly, the present invention relates to the use in cell adhesion and wound healing of peptides containing one or more copies of the $2^{nd}$ and/or $4^{th}$ fas-1 domain of βig-h3, said $2^{nd}$ and $4^{th}$ domains sharing a high homology in two amino acids, aspartic acid and isoleucine, essential for binding to integrin and thus mediating cell adhesion. Also, the present invention is concerned with an expression system for the peptides useful in cell adhesion and wound healing.

BACKGROUND OF THE INVENTION

βig-h3 is an extracellular matrix protein whose expression is induced in various cell lines, including human melanoma cells, mammary ephithelial cells, keratinocytes, and lung fibroblasts, following signaling by active TGF-β (Skonier, J. et al., DNA Cell Biol. 13, 571, 1994). The βig-h3 gene was first isolated by differential hybridization screening of a cDNA library made from a human lung adenocarcinoma cell line that had been treated with TGF-β. βig-h3 gene encodes a 683-amino acid protein that is highly conserved between species. It contains an N-terminal secretory signal peptide and an Arg-Gly-Asp (RGD) motif at the C-terminus. The RGD motif is found in many extracellular matrix proteins modulating cell adhesion and serves as a ligand recognition sequence for several integrins (Stonier, J. et al., DNA Cell Biol., 11, 511, 1992).

According to several studies, βig-h3 is known to be involved in cell growth and proliferation, wound healing, and cell adhesion, although the underlying mechanisms for these functions are still unclear. However, βig-h3 seems to play an important role in the morphogenesis and interactions with cells and extracellular matrix proteins in various tissues.

Some evidence related to the role of βig-h3 in mediating cell attachment and detachment is provided by several studies. For example, purified βig-h3 protein is found to promote the attachment and spreading of skin fibroblasts while inhibiting the adhesion of A549, HeLa and Wi-38 cells in serum-free media. Particularly, βig-h3 is known to have inhibitory activity against tumor cell growth, and to affect colony formation and morphology. The inhibitory activity was demonstrated by the report in which transfection of βig-h3 expression plasmids into CHO (Chinese hamster ovary) cells led to marked decreases in cell proliferation and the ability of these cells to form tumors in nude mice. Further, a wound healing method was developed on the basis of the finding that application of a pharmaceutically effective amount of βig-h3 to wounds makes cells, especially fibroblasts, spread over and adhere to the wound site. Consequently, βig-h3, a cell adhesion molecule induced by TGF-β in various cell lines, plays a very important role in cell growth, cell differentiation, wound healing, morphogenesis and cell adhesion (Rawe, I. M. et al., Invest. Ophthalmol. Vis. Sci. 38, 893, 1997; Lebaron, R. G. et al., J. Invest. Dermatol. 104, 844, 1995).

βig-h3 contains four 140 amino acid repeats with internal homology, namely fas-1 domains. The internal repeat domains have highly conserved sequences found in secretory proteins or membrane proteins of various species, including mammals, insects, sea urchins, plants, yeasts, and bacteria. Proteins containing the conserved sequence are exemplified by periostin, fasciclin I, sea urchin HLC-2, algal-CAM and mycobacterium MPB70. The conserved domain in these proteins (hereinafter referred to as "fas-1") consists of about 110 to 140 amino acids with two highly conserved branches, H1 and H2, of about 10 amino acids each (Kawamoto, T. et al., Biochem. Biophys. Acta. 1395, 288, 1998).

Four fas-1 domains are found in βig-h3, periostin, and fasciclin I, two fas-1 domains in HLC-2, and only one fas-1 domain in MPB70. Although the functions of the proteins are not elucidated clearly, some of them are known to act as cell adhesion molecules. For instance, βig-h3, periostin, and fasciclin 1 are reported to mediate the adhesion of fibroblasts, osteoblasts, and nerve cells, respectively. Also, it is disclosed that algal-CAM is a cell adhesion molecule present in embryos of the algae Volvox (LeBaron, R. G., et al., J. Invest. Dermatol. 104, 844, 1995; Horiuchi, K. et al., J. Bone Miner. Res. 14, 1239, 1999; Huber, O. et al., EMBO J. 13, 4212, 1994).

At first, it was believed that the cell attachment activity of βig-h3 would be mediated by the C-terminal RGD motif. However, some research results revealed that the RGD motif is not necessary for promoting the spreading of chondrocytes and that the mature soluble βig-h3 whose RGD motif is deleted by carboxyl-terminus processing is able to inhibit cell adhesion, leading to the conclusion that the RGD motif of βig-h3 is dispensable for mediating the cell attachment activity of βig-h3. In addition, it has been recently reported that βig-h3 promotes the spreading of fibroblasts via integrin α1β1 whereas the RGD motif of βig-h3 is not necessary for mediating the cell adhesion property of βig-h3. According to a recent report, βig-h3 binds specifically to integrin to enhance the cell adhesion and spreading of cells irrespective of RGD motif (Ohno, S. et al., Biochm. Biophys. Acta 1451, 196, 1999). Further, the conserved peptides H1 and H2 of βig-h3 were found to have no influence on βig-h3-mediated cell adhesion. These results, taken together, indicate that amino acids indispensable for the cell attachment activity of βig-h3 exist somewhere other than the H1 and H2 regions. A computer search based on homologies not only among the repeated fas-1 domains of βig-h3 but also among fas-1 domains of other proteins revealed that there are a few highly conserved amino acids in addition to H1 and H2 peptides, suggesting the possibility of the involvement of the conserved amino acid sequences in the cell attachment activity.

Of the domains of βig-h3, known to play an important role in cell adhesion, either of the $2^{nd}$ or $4^{th}$ domain is identified as a minimum domain essential for the cell adhesion of the molecule in accordance with the present invention. Based on these findings, recombinant proteins containing the essential functional domains are also identified as being effective for wound healing, in accordance with the present invention.

Recent research for wound healing has been subdivided into cell biology and molecular biology and the promotion of wound healing has had increasing applications in various clinical fields. However, cell biological and molecular biological mechanisms of wound healing still remain unclear. According to findings disclosed thus far, wound healing is a tissue response to trauma, leading to tissue repair through complex biological processes, including chemotaxis, cell differentiation and replication, matrix protein synthesis, angiogenesis, and wound reconstitution (Steed, D. L., et al., Clin. Plast. Surg. 25, 397, 1998).

Growth factors are representative materials that appear in the early stage of the wound healing process and control the subsequent wound healing process. Having strong influence over all stages of wound healing, growth factors act to control the growth, differentiation and metabolism of cells and reorganize the environs of the wound by their chemotactic properties which attract various cells types that are involved in inflammation and tissue repair, cellular proliferation, stimulating angiogenesis and the synthesis and degradation of the extracellular matrix. PDGF (platelet-derived growth factor) attracts fibroblasts to the wound and stimulates them to proliferate, and transforming growth factor-beta (TGF-β) causes them to make collagen. PDGF is chemotactic for most cells involved in wound healing, stimulates angiogenesis, remodeling and contraction, and activates wound healing cells (Mustoe, T. A. et al., J. Clin. Invest. 87, 694, 1991; Lepisto, J. et al., J. Surg. Res. 53, 596, 1992). EGF (epidermal growth factor) stimulates keratinocyte migration, angiogenesis and granulation tissue development and activates mitogenesis of keratinocyets and fibroblasts (Franklin, J. D. et al., Plast. Recsonst. Surg. 64, 766, 1979; Buckly, A. et al., Proc. Natl. Acad. Sci. USA, 82, 7340, 1985). bFGF (basic fibroblast growth factor) stimulates angiogenesis, epithelialization, and collagenous fiber deposition, and associates with heparin in various forms to perform relevant functions (Tsuboi, R. et al., J. Exp. Med. 172, 245, 1990; Kinsnorth, A. N. et al., Br. J. Surg. 77, 409, 1990). IGF (insulin-like growth factor) enhances cell differentiation. VEGF (vascular endothelial growth factor) increases vasopermeability and promotes endothelial mitogenesis.

Of the growth factors and cytokines involved in wound healing, TGF-β is the most representative. Existing in three forms (TGF-β1, TGF-β2 and TGF-β3) in mammals, the cytokine plays important roles in the growth and differentiation of various cells and has various complex functions, including control of cell growth, regulation of immune responses, stimulation of osteogenesis, induction of cartilage specific macromolecules, and promotion of wound healing (Bennett, N. T. et al., Am. J. Surg. 165, 728, 1993). Appearing in the ephithelium during wound healing, TGF-β is believed to stimulate the expression of integrin within keratinocytes during re-epithelialization. In recent research into TGF-β expression, it was revealed that TGF-β3 mRNA is expressed in the epithelia of normal skin and acute and chronic wounds, while TGF-β1 mRNA is not expressed in normal skin and chronic wounds, but expressed in the epithelial layer regenerated from acute wounds, and nowhere is expressed TGF-β2 mRNA (Schmid, P. et al., J. Pathol. 171, 191, 1993). Based on the effects, even though their mechanisms are not firmly established, TGF-β is expected to play a major role in re-epithelialization.

Expression of βig-h3 is up-regulated by TGF-β, suggesting that βig-h3 is involved in the mediation of some signals of TGF-β. CHO (Chinese hamster ovary) cells transformed with βig-h3 expression plasmids are reported to show decreased tumorigenic ability (Skonier, J. et al., DNA Cell Biol. 13, 571, 1994). In contrast, βig-h3 expression is down-regulated in dexamethasone-treated stem cells, some tumor cells and the fibroblasts cultured from the skin lesion sites afflicted with localized hyperostosis of melorheostosis. βig-h3 is also reported to serve as a negative regulator of osteogenesis (Genini, M. et al., Int. J. Cancer 66, 571, 1996; Schenker, T. et al., Exp. Cell. Res. 239, 161, 1998; Kim, J. et al., J. Cell Biochem. 77, 169, 2000). In addition to these functions, βig-h3, known as a cell adhesion molecule, promotes the adhesion and spreading of fibroblasts in the dermis. According to studies into the distribution of βig-h3 in eye tissues, it is reported that the adhesion molecule is expressed in corneal epithelia of normal adults, intracorneal fetal stromal cells, and the endothelial and stromal cells in the process of wound healing. In addition, βig-h3 is expressed in the juxtaglomerular apparatus and proximal tubules of the kidneys, and its expression is increased in diabetes mellitus. Further, it is found in subendothelial smooth muscles of the coronary arteries of normal persons, and its amount is increased in the endometria of blood vessels in the case of arteriosclerosis. However, the expression of βig-h3 in normal dermal tissues and dermal wounds has not yet been firmly established (Klintworth, G. K. et al., Am. J. Pathol. 152, 743, 1998; Munier, F. L. et al., Nature Genetics 15, 247, 1997; Streeten B. W. et al., Arch. Ophthalmol. Vis. Sci. 38, 893, 1997). As mentioned above, the distribution and expression of βig-h3 in normal human tissues remains unclear. Particularly, there are no reports regarding expression patterns of βig-h3 in dermal wounds. However, some research groups have reported that βig-h3 functions to promote the adhesion and spreading of dermal fibroblasts, so that it is expected to make a contribution to the promotion of wound healing.

SUMMARY OF THE INVENTION

With the background in mind, the intensive and thorough research on βig-h3-mediated cell adhesion, leading to the present invention, resulted in the finding that there exist highly conserved amino acid sequences, in addition to H1 and H2 motifs, among fas-1 domains of βig-h3 and among fas-1 domains of other peptides, as analyzed by computer search, and particularly, high homology is detected at aspartic acid and isoleucine residues at positions near the H2 region. In addition, the $2^{nd}$ and $4^{th}$ domains of βig-h3, each containing the conserved amino acid residues, were found to induce cell adhesion through α3β1 integrin. Further, recombinant proteins which were designed to have the $2^{nd}$ and/or $4^{th}$ fas-1 domain of βig-h3 were identified as being identical to wild type βig-h3 in cell attachment and spreading activity and wound healing effect.

Therefore, it is an object of the present invention to provide peptides which contain conserved amino acid sequences essential for cell attachment, spreading and detachment activity.

It is another object of the present invention to provide the use of the peptides in cell adhesion and wound healing.

It is a further object of the present invention to provide an expression system for the peptides.

It is still a further object of the present invention to provide a method for attaching cells.

It is still another object of the present invention to provide a method for healing wounds.

In accordance with an aspect of the present invention, there is provided a recombinant protein, comprising a portion of domains of βig-h3, useful in mammalian cell attachment.

In accordance with another aspect of the present invention, there are provided expression vectors pβig-h3 D-II, pβig-h3 D-IV, and pβig-h3 D-IV 4X, capable of expressing the $2^{nd}$ and $4^{th}$ fas-1 domain of human βig-h3 corresponding to amino acids 237-377 (SEQ ID NO:24) and 498-637 (SEQ ID NO:26), respectively.

In accordance with a further aspect of the present invention, there are provided novel E. coli strains, transformed with the expression vectors pβig-h3 D-II, pβig-h3 D-IV, and pβig-h3 D-IV 4X, deposited at the Korean Collection for Type Cultures #52, Oun-dong, Yusong-ku, Taeon 305-333, Republic of Korea, identified as *E. coli* BL21/Hisβ-g (accession No. KCTC 0905BP, deposited Dec. 7, 2000), *E. coli* BL21/Hisβ-e (accession No. KCTC 0904BP, deposited Dec. 7, 2000), and *E. coli* BL21/Hisβ-e4x (accession No. KCTC 0906BP, deposited Dec. 7, 2000), respectively.

In accordance with still a further aspect of the present invention, there is provided a method for attaching cells, comprising the steps of: preparing a recombinant protein containing one or more copies of the $2^{nd}$ and/or $4^{th}$ domain of βig-h3, by use of an expression vector; coating the recombinant protein onto a solid support; and applying cells to the protein-coated solid support.

In accordance with still another aspect of the present invention, there is provided the use of the recombinant protein in cell attachment.

In accordance with yet another aspect of the present invention, there is provided the use of the recombinant protein in wound healing.

In accordance with still yet another aspect of the present invention, there is provided a method for healing wounds, comprising the steps of: coating a solid support with a recombinant protein containing one or more copies of the $2^{nd}$ and/or the $4^{th}$ domain of βig-h3; attaching skin cells to the solid support; and applying the solid support to wounds.

BRIEF DESCRIPTION OF THE DRAWINGS

FIG. 4 shows curves in which the HCE cell adhesion and spreading activities of the recombinant proteins βigh3-WT and βigh3-ΔRGD are found to be concentration-dependent as measured by the count (A) and surface area (B) of attached cells.

FIG. 5 shows histograms in which the HCE cell adhesion activities of the recombinant proteins βigh3-WT and βigh3-ΔRGD are compared in terms of count (A) and surface area (B) of attached cells.

FIG. 11 shows parts of amino acid sequences (SEQ ID NOS: 1 to 21) of various matrix proteins containing fas-1 domains.

FIG. 21 shows optical photographs of wounds whose areas are reduced after being treated with a chitosan base alone (A) and in combination with fibronectin (B), βig-h3 3X (C), and βig-h3 4X (D).

DETAILED DESCRIPTION OF THE INVENTION

Figure 1:
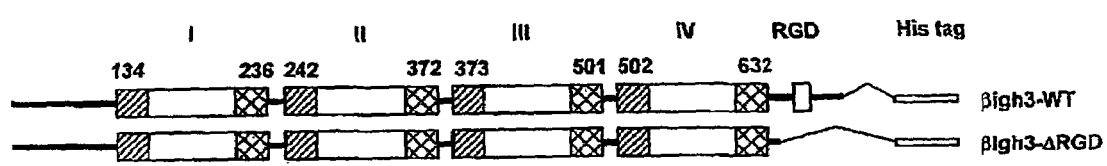
FIG. 1 is a schematic diagram showing recombinant proteins βigh3-WT and βigh3-ΔRGD, wherein conserved regions are represented by ▨ and ▩, and RGD motif by ®.

In the present invention, recombinant proteins are prepared on the basis of the $2^{nd}$ and $4^{th}$ fas-1 domains of βig-h3 and used alone or in combination, for cell adhesion and spreading. To select the $2^{nd}$ and $4^{th}$ domains, the domains of βig-h3 active in cell adhesion and spreading was identified. To this end, the C-terminal sequence Arg-Gly-Asp (RGD), known as a ligand recognition sequence for several integrins, was examined for its effect on the cell adhesion property of βig-h3. The cell attachment activity was measured using the number and surface area of attached cells. As a result, βig-h3 was found to promote cell adhesion and spreading, independent of the RGD motif.

Based on this finding, chemical reagents were used to address the specificity of cell adhesion activity of βig-h3 and to get further clues about the nature of the cell surface receptor for βig-h3. The data obtained from the use of chemical reagents suggest that the cell surface receptor for βig-h3, which is involved in the cell adhesion activity of βig-h3, could be one of the RGD-dependent integrins, which require divalent cations for interaction with βig-h3.

Next, to identify minimum domains essential for the cell adhesion function of βig-h3, an examination was made of the ability of each fas-1 domain to mediate cell adhesion.

This examination was based on the fact that fas-1 domains are found in various cell adhesion molecules, such as βig-h3, periostin, fasciclin I, HLC-2, and algal-CAM and the number of fas-1 domains present in such adhesion molecules varies from protein to protein. This fact led to the inference that all four fas-1 domains might not be required for the cell adhesion activity of βig-h3 and in an extreme case, only one domain could mediate the cell adhesion activity of βig-h3. In the present invention, the either of $2^{nd}$ or $4^{th}$ fas-1 domain of βig-h3 is revealed to be sufficient for the cell adhesion function of βig-h3. These results lead to the conclusion that the H1 and H2 sequences, common in the four domains of βig-h3, are not essential for the mediation of the cell adhesion activity of βig-h3. Additionally, two amino acids, that is, aspartic acid and isoleucine at positions near the H2 region within the $2^{nd}$ and $4^{th}$ fas-1 domains, were found to be highly conserved, implying that these amino acid residues constitute a cell adhesion-related motif. The indispensability of the two conserved amino acids for cell adhesion was identified using substitution mutants of the $4^{th}$ fas-1 domain of βig-h3.

In another embodiment of the present invention, a wound healing method is provided in which the $2^{nd}$ and $4^{th}$ fas-1 domains of βig-h3 are used, individually or in combination.

An comparison was made of wound healing effects of mutant βig-h3 proteins containing cell adhesion-active domains only and those of wild type βig-h3 (βig-h3-WT) containing domains a portion of the domains. In this regard, recombinant proteins containing the cell adhesion-active domains were applied to rats.

When a recombinant protein containing the $4^{th}$ fas-1 domain of βig-h3 was used a pharmaceutically effective ingredient for an ointment, wound shrinkage was observed, in addition to re-epithelialization and collagenous fiber formation. Ultimately, these results mean that one of the $2^{nd}$ or $4^{th}$ fas-1 domain of βig-h3, in which the conserved aspartic acid and isoleucine exist, is useful for wound healing and thus can be utilized for the development of therapeutics for wounds.

Also, excellent cell adhesion and wound healing effects were obtained using a recombinant protein containing the $2^{nd}$ fas-1 domain of βig-h3 or $2^{nd}$ and $4^{th}$ domains.

Over the protein containing all of the domains, recombinant proteins containing parts of the domains have an advantage in that they can be produced in larger quantities because they are synthesized in water-soluble forms and thus do not undergo denaturation.

EXAMPLES

A better understanding of the present invention may be obtained in light of the following examples which are set forth to illustrate, but are not to be construed to limit the present invention.

Example 1

Identification of Cell Adhesion Activity of RGD-Independent βig-h3 Proteins 1-1: Production of Recombinant βig-h3 Protein In order to find the domains of βig-h3 which have, in practice, cell adhesion and spreading activity, the C-terminal sequence Arg-Gly-Asp (RGD), known as a ligand recognition sequence for several integrins, was examined for effect on the cell adhesion property of βig-h3. In this regard, an RGD-deleted human recombinant βig-h3 protein (βigh3-ΔRGD) and a wild-type human recombinant βig-h3 protein (βigh3-WT, SEQ ID NO: 22) were prepared.

First, the full-length human βig-h3 cDNA cloned in pBluescript (pBsβig-h3) was digested with NdeI and BglII. The DNA fragment was subcloned into the EcoRV-EcoR1 site of pET-29b(+) (Novagen Inc.). Human βigh3-WT was prepared by introducing a 1351 bp NcoI fragment excised from βig-h3 cDNA into the NcoI site of this clone. βigh3-ΔRGD was derived from βigh3-WT by cutting out a 3'-fragment of the βigh3-WT plasmid with AoCI and NotI followed by blunting and self ligation, as shown in FIG. 1.

Figure 2:
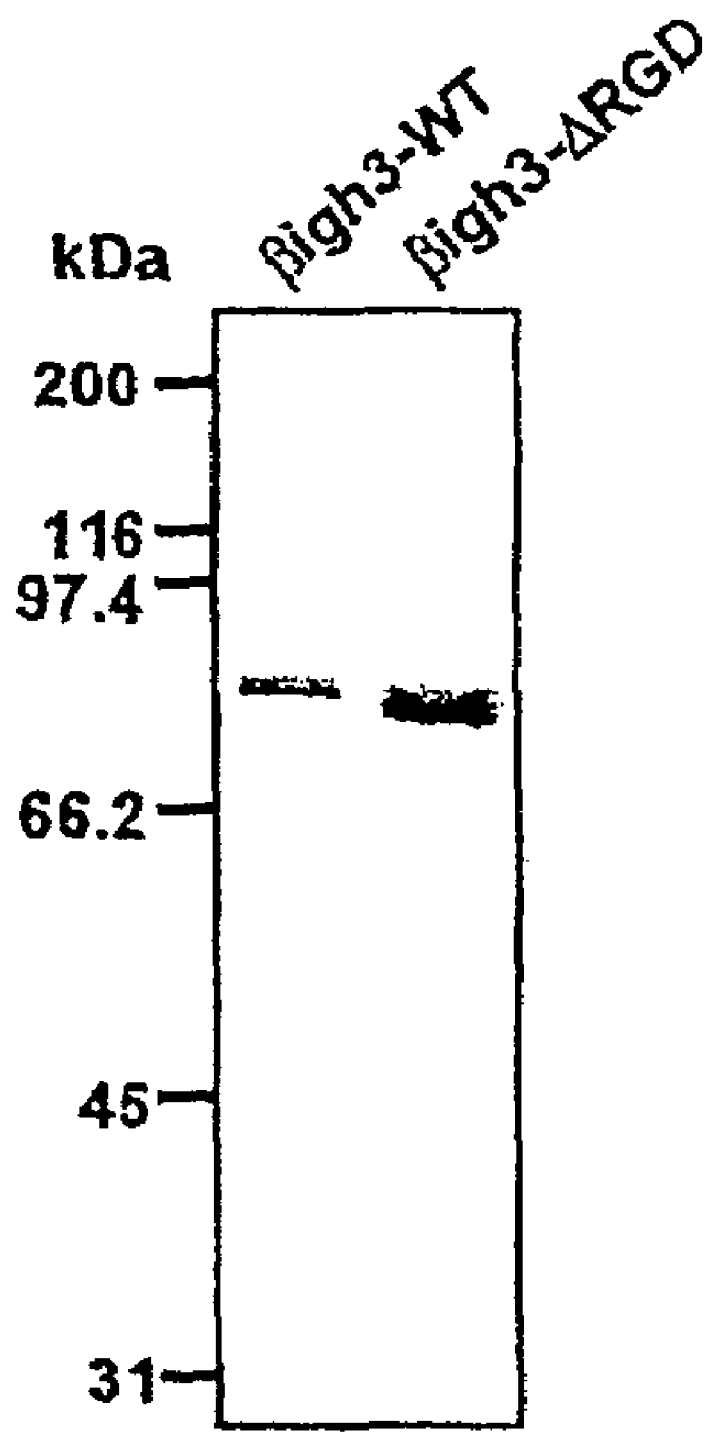
FIG. 2 is a photograph showing SDS-PAGE results of recombinant proteins βigh3-WT and βigh3-ΔRGD.

After being transformed with each recombinant plasmid, *E. coli* BL 21 DE3 was cultured in LB medium containing 50 μg/ml kanamycin at 37° C. until the optical density (OD) at 595 nm reached 0.5-0.6. The recombinant βig-h3 proteins were induced using 1 m isopropyl-β-D-(−)-thiogalactopyranoside (IPTG) at 37° C. for 3 hours. The pellet thus obtained was resuspended in a lysis buffer (50 mM Tris-HCl (pH 8.0), 100 mM NaCl, 1 mM EDTA, 1% Triton X-100, 1 mM PMSF, 0.5 mM DTT) and then sonicated. The inclusion bodies were dissolved in a denaturation buffer of 8 M urea containing 20 mM, followed by the purification of the denatured proteins with the aid of Ni-NTA resin (Qiagen). The recombinant proteins were eluted with 200 mM imidazole solution and then dialyzed sequentially from high to low urea in 20 mM Tris-HCl buffer containing 50 mM NaCl. These recombinant proteins were analyzed using SDS-PAGE, as shown in FIG. 2.

1-2: Assay for the Cell Adhesion Activity of Recombinant βig-h3 fas-1 Domain Proteins Human corneal epithelial (HCE) cells used in this assay were cultured in DMEM (EMEM/F-12, Gibco BRL) supplemented with 15% fetal bovine serum, Gentamicin (40 μg/ml), insulin (5 μg/ml), cholera toxin (0.1 μg/ml) and human epidermal growth factor (hEGF) at 37° C. in 5% $CO_2$.

The cell adhesion assay was performed as follows. First, the recombinant βig-h3 proteins or other extracellular matrix proteins were let to adhere to the bottoms of 96-well microculture plates (Falcon) by incubation at 37° C. for 1 hour and blocked with PBS containing 0.2% BSA. The coated extracellular matrix proteins were human plasma vitronectin (Promega), purified human plasma fibronectin (pFN), chicken collagen types I and II (Chemicon International Inc.), bovine collagen types IV and VI (Chemicon), mouse laminin (Chemicon), and bovine serum albumin (BSA) (Sigma). Cells were trypsinized and suspended in the culture media at a density of $2 \times 10^5$ cells/ml. 0.1 ml of the cell suspension was added to each well of the plates coated with the recombinant proteins.

Following incubation at 37° C. for 1 hour, unattached cells were removed by rinsing with PBS. Attached cells were incubated for 1 hour at 37° C. in 50 mM citrate buffer, pH 5.0, containing 3.75 mM p-nitrophenol-N-acetyl 1-β-D-glycosaminide as a hexosaminidase substrate and 0.25% Triton X-100, followed by the addition of 50 mM glycine buffer, pH 10.4, containing 5 mM EDTA to block the enzyme activity. A measurement was made of absorbance at 405 nm in a Multiskan MCC/340 microplate reader.

To determine cell area as an index for cell adhesion activity, $4 \times 10^4$ cells were applied to substrates in 48-well culture plates. The attached cells were fixed weith 8% glutaraldehyde (Sigma) and then stained with 0.25% Crystal Violet (Sigma) in 20% methanol. Measurement of cell areas was performed by Image-Pro plus software (Media Cybernetics). Experiments were repeated in triplicate with 200 or 300 measurements per site for each experiment. Data is reported as the mean area at specific time points±standard error of mean.

Figure 3:
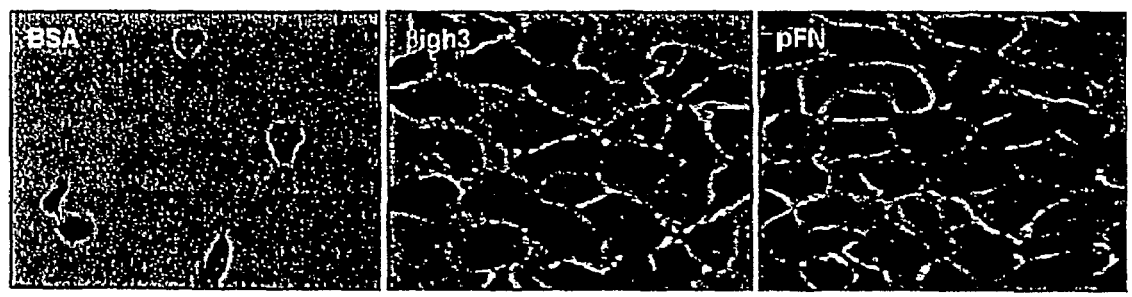
FIG. 3 is a microphotograph showing HCE cell adhesion and spreading effects of recombinant proteins βigh3-WT and βigh3-ΔRGD after dying with crystal violet.

As a result of the measurement of cell adhesion and spreading activity using βigh3-WT and βigh3-ΔRGD, the numbers and surface areas of HCE cells which adhered to βigh3WT were clearly greater than those attached to albumin serving as a negative control, and were comparable to those of cells which adhered to fibronectin as shown in FIG. 3. The cell adhesion and spreading activities of βig-h3 were concentration-dependent, as shown in FIGS. 4A and 4B). βig-h3ΔRGD lacking the RGD motif was almost equally effective at supporting cell adhesion and spreading (FIGS. 5A and 5B). These results, taken together, confirm that βig-h3 supports cell adhesion and spreading, independent of the RGD motif.

Experimental Example 1

Identification of Cell Surface Receptor of βig-h3 Involved in Cell Adhesion Activity of βig-h3

1-1: Identification of Cell Adhesion Activity Using Matrix Peptide and Reagent

In order to identify cell surface receptors involved in the cell adhesion activity of βig-h3 protein, an inhibition assay was performed using various reagents.

Initially, plastic culture dishes were coated with 10 μg/ml fibronectin, βigh3-WT or βigh3-ΔRGD. HCE cells were preincubated for 30 min in media containing 5 mM EDTA, 100 μg/ml βigh3-WT, 100 μg/ml βigh3-ΔRGD, 1 mM RGD, 1 mM RGE or 100 μg/ml fibronectin, or none of them, and then assayed for cell adhesion as in Example 1.

Figure 6A:
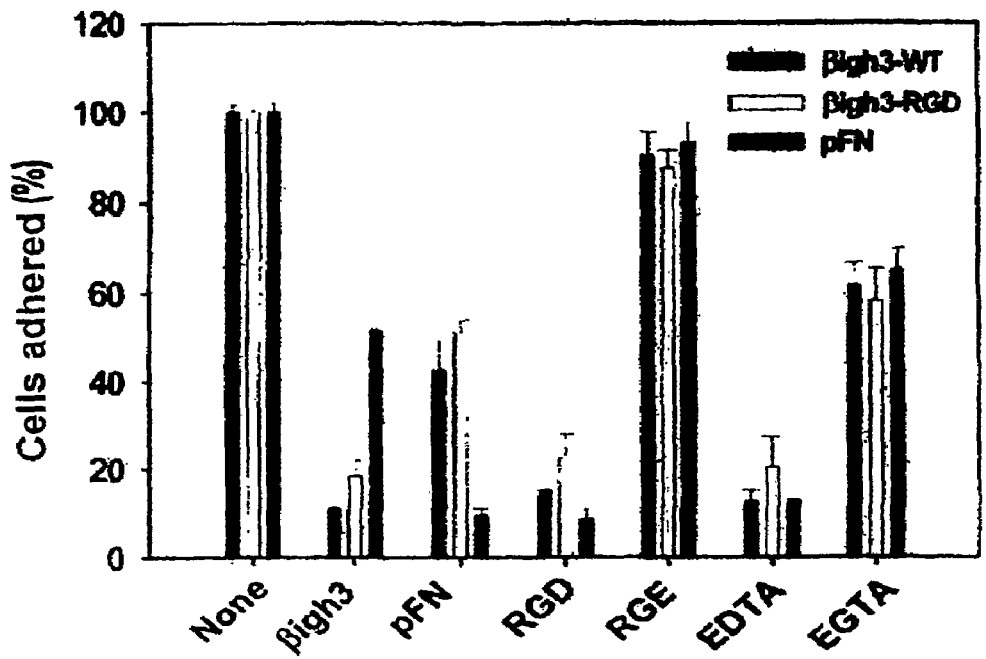
FIG. 6a is a histogram showing effects of various compounds on the HCE cell adhesion activities of the recombinant proteins βigh3-WT and βigh3-ΔRGD.

Cell adhesion to βig-h3 was significantly inhibited by βig-h3 itself, RGD peptide and EDTA, and partially inhibited by fibronectin and EGTA, while being not inhibited by RGE peptide. Cell adhesion to fibronectin was also significantly inhibited by fibronectin itself, RGD peptide and EDTA, and partially inhibited by βig-h3 and EGTA, but not by RGE peptide, as shown in FIG. 6A. These results indicate that the cell surface receptor for βig-h3, which is involved in the cell adhesion activity of βig-h3, could be one of the RGD-dependent integrins.

1-2: Effect of Divalent Cations on Cell Adhesion Activity

To analyze the divalent cation sensitivity of βig-h3-mediated adhesion, cells were suspended in HEPES-buffered saline (HBS) (150 mM NaCl, 25 mM HEPES, 2 mM EDTA, pH 7.4) at a density of $2 \times 10^5$ cells/ml and incubated at 37° C. for 30 min. Then, they were washed twice in HBS and resuspended in the same buffer. Aliquots of cells (50 μl) were then added to the microculture plate wells and incubated for 30 min at 37° C. in a humidified atmosphere of 5% $CO_2$ with 50 μl aliquots of HBS containing divalent cations ($MnCl_2$, $MgCl_2$ or $CaCl_2$) at a concentration twice as large as the final concentration. Subsequently, they were plated on ligand-coated dishes to perform the adhesion assay.

Figure 6B:
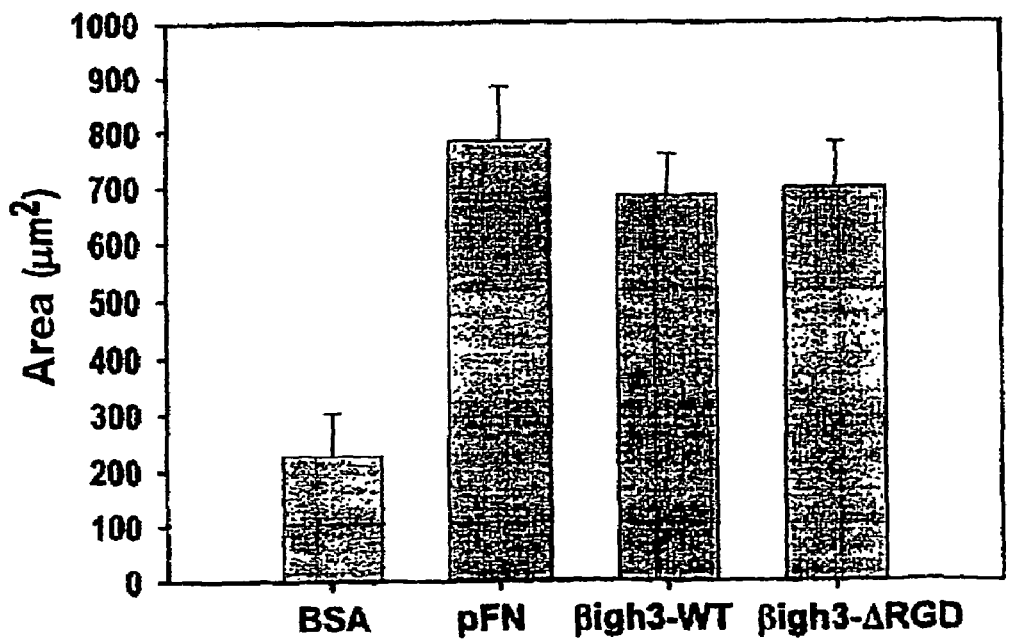
FIG. 6b is a histogram showing effects of divalent cations on the HCE cell adhesion activities of the recombinant protein βigh3-WT.

Cell adhesion to βig-h3 was strongly promoted by $Mn^{2+}$, and to a lesser extent by $Mg^{2+}$, but only marginally by $Ca^{2+}$, as shown in FIG. 6B. taken together, the results demonstrate that the cell surface receptor of βig-h3 is a kind of RGD-dependent integrin which requires divalent cations for interaction with βig-h3.

1-3: Identification of Cell Surface Receptor of βig-h3 Using Monoclonal Antibody Against Integrin To identify receptors for βig-h3, function-blocking monoclonal antibodies to integrin subunits were examined for their effect on the adhesion of HCE cells to a surface coated with βig-h3. In this regard, initially, HCE ($3 \times 10^5$ cells/ml) were preincubated in an incubation solution in the presence of each of the monoclonal antibodies (5 μg/ml) against different types of integrins at 37° C. for 30 min. The preincubated cells were transferred onto plates precoated with βig-h3 proteins and then incubated further at 37° C. for 1 hour, followed by the quantitative analysis of βig-h3 binding with hexosaminidase substrate. The values are expressed as percentages of the number of cells adhering to βig-h3 in the absence of monoclonal antibodies.

Figure 6C:
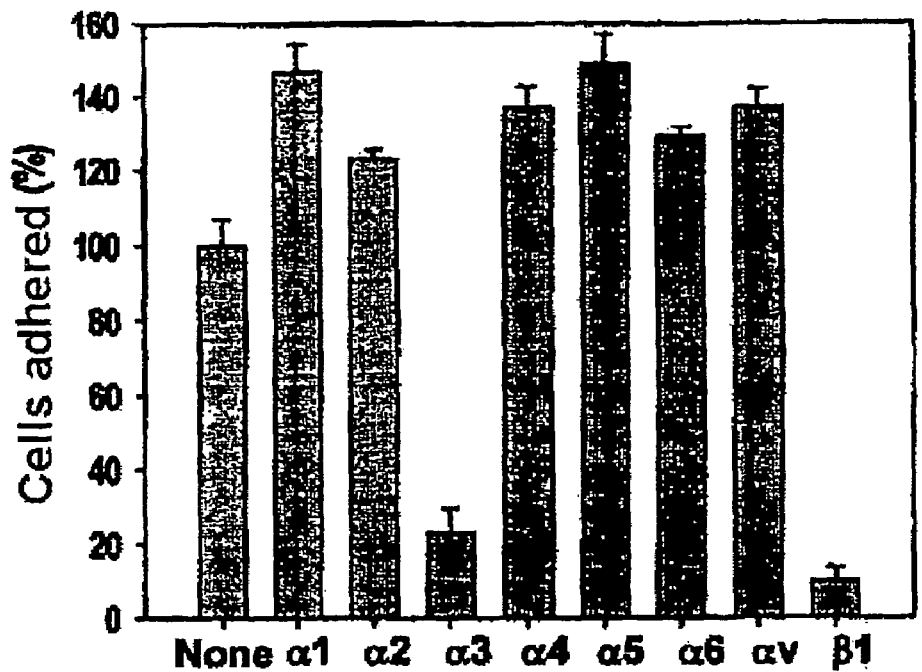
FIG. 6c is a histogram showing the inhibition effect of anti-integrin monoclonal antibody on the HCE cell adhesion activity of the recombinant protein βigh3-WT.

Adhesion to the βig-h3 coated surface was specifically inhibited by antibody against α3 subunit. Because the integrin α3 subunit is known to couple with the integrin β1 subunit, anti-β1 antibody significantly blocked cell adhesion to βig-h3, as shown in FIG. 6C. Similar results were observed using HT1080 cells.

As a control experiment for the function-blocking antibodies, fibronectin, vitronectin, laminin and type I collagen were employed as substrata. HCE cells were preincubated with function-blocking monoclonal antibodies to integrin subunits and then transferred onto wells coated with 10 μg/ml fibronectin, vitronectin, type I collagen or laminin. Following incubation, cell counts of adhered cells were analyzed.

Figure 6D:
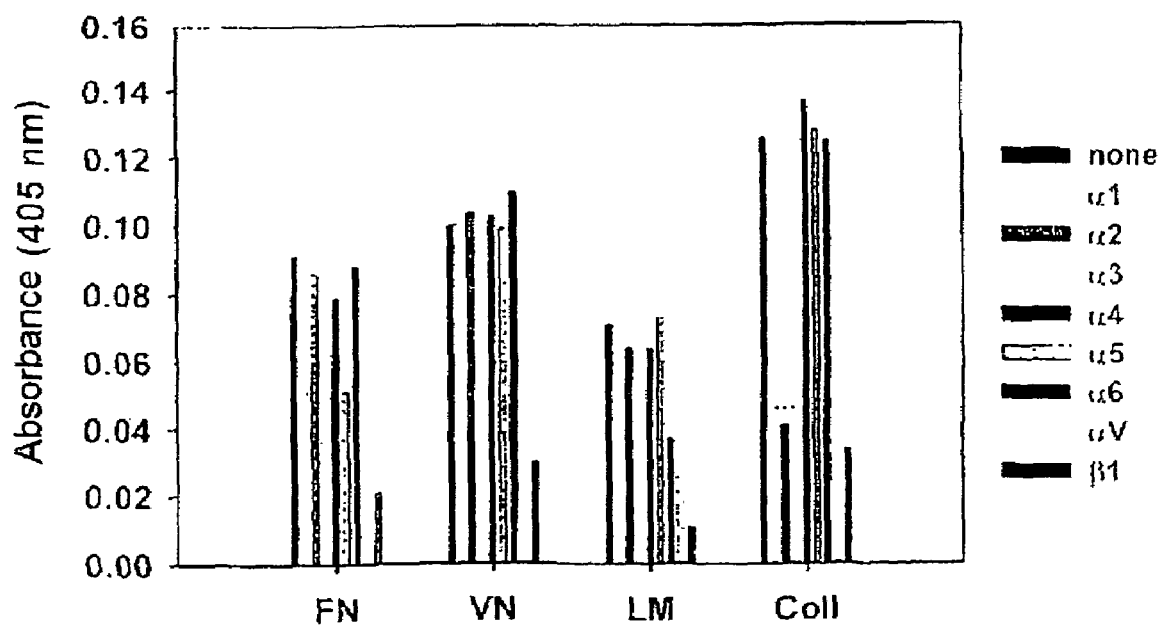
FIG. 6d is a histogram showing the inhibitory effect of anti-integrin monoclonal antibody on the HCE cell adhesion activities of various proteins.

Cell adhesion to fibronectin was shown to be clearly inhibited by antibodies to integrins α3 and α5. Adhesion to vitronectin and type I collagen was blocked by antibodies to integrin αv and α2, respectively, whereas cell adhesion to laminin was inhibited by antibodies to integrins α3 and α6, as shown in FIG. 6D. On the other hand, antibody to β1 integrin efficiently inhibited cells from adhering to all ligands mentioned above.

Figure 6E:
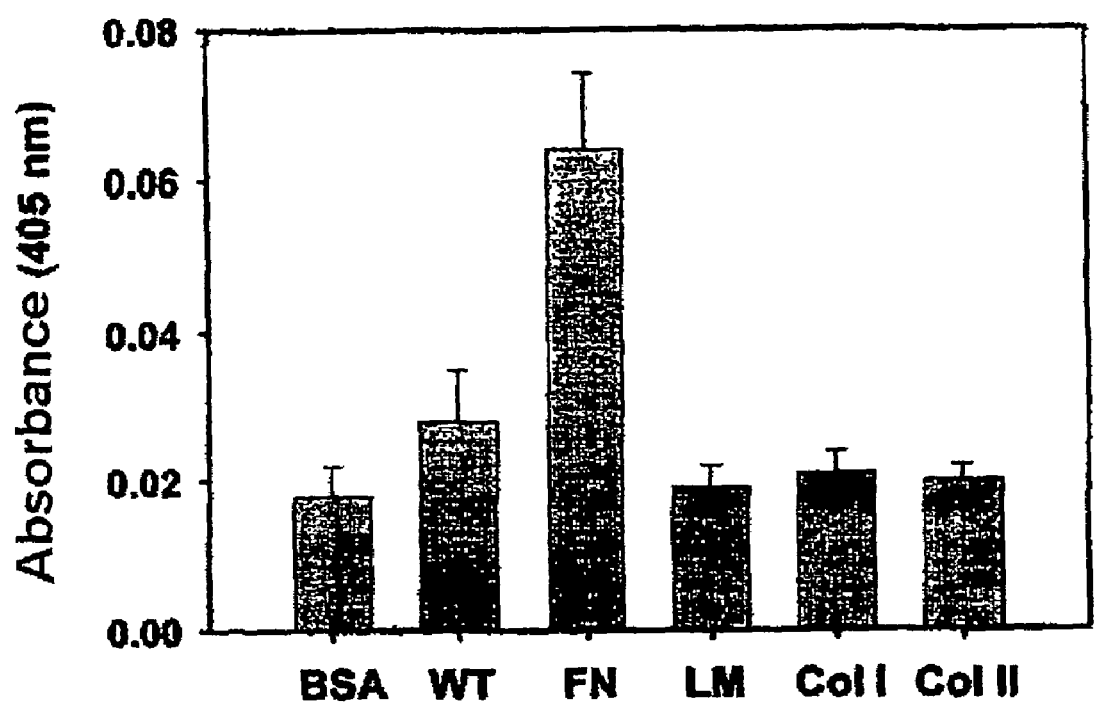
FIG. 6e is a histogram showing adhesion specificity of K562 cells for the recombinant protein βigh3-WT and matrix proteins.

For another control experiment, K562 cells, known to express α5, but not α3 integrin, were used. K562 cells were inoculated onto plates coated with βigh3-WT, fibronectin, laminin, or type I collagen and incubated for 1 hour, followed by the hexosaminidase analysis. K562 cells did not adhere to βig-h3, but adhered to fibronectin and vitronectin. Taken together, these results suggest integrin α3β1 is a specific receptor for βig-h3 in HCE cells, as shown in FIG. 6E.

Example 2

Identification of Domains Essential to Cell Adhesion Activity of βig-h3

In an attempt to identify essential amino acids conferring cell adhesion activity of βig-h3, an examination was made to determine whether each repeat domain is capable of mediating cell adhesion.

Figure 7:
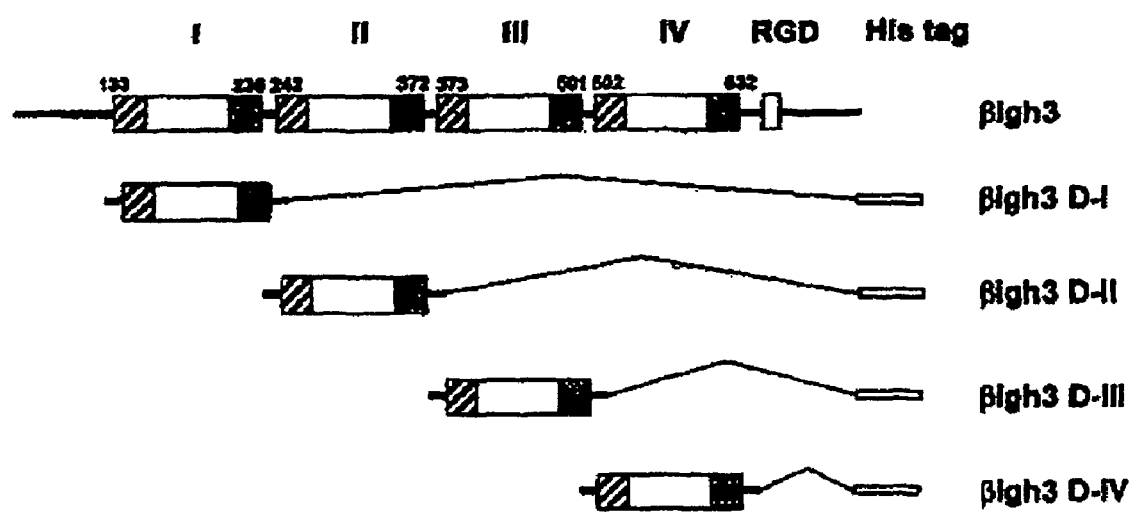
FIG. 7 is a schematic diagram showing recombinant proteins having each of the fas-1 domains of βig-h3.

Four recombinant proteins corresponding respectively to four repeat domain were prepared: four βig-h3 cDNA fragments encoding a polypeptide corresponding $1^{st}$ fas-1 domain having amino acid sequence of 129-241 (SEQ ID NO:23), a polypeptide corresponding $2^{nd}$ fas-1 domain having amino acid sequence of 237-377 (SEQ ID NO:24), a polypeptide corresponding $3^{rd}$ fas-1 domain having amino acid sequence of 368-506 (SEQ ID NO:25), and a polypeptide corresponding $4^{th}$ fas-1 domain having amino acid sequence of 498-637 (SEQ ID NO:26), respectively, were amplified by PCR and cloned into the EcoRV-XhoI site of pET-29b(+) and the resulting four expression vectors, named pβig-h3 D-I, pβig-h3 D-II, pβig-h3 D-III, and pβig-h3 D-IV, were used to prepare the recombinant proteins, as shown in FIG. 7. E. coli transformants with the expression vectors pβig-h3 D-II and pβig-h3 D-IV were designated E. coli BL21/Hisβ-g and E.coli BL21/Hisβ-e and deposited in the Korean Collection for Type Culture of Korea Research Institute of Bioscience and Biotechnology (KRIBB) with accession Nos. KCTC 0905BP and KCTC 0904BP, respectively, on Dec. 4, 2000.

Figure 8:
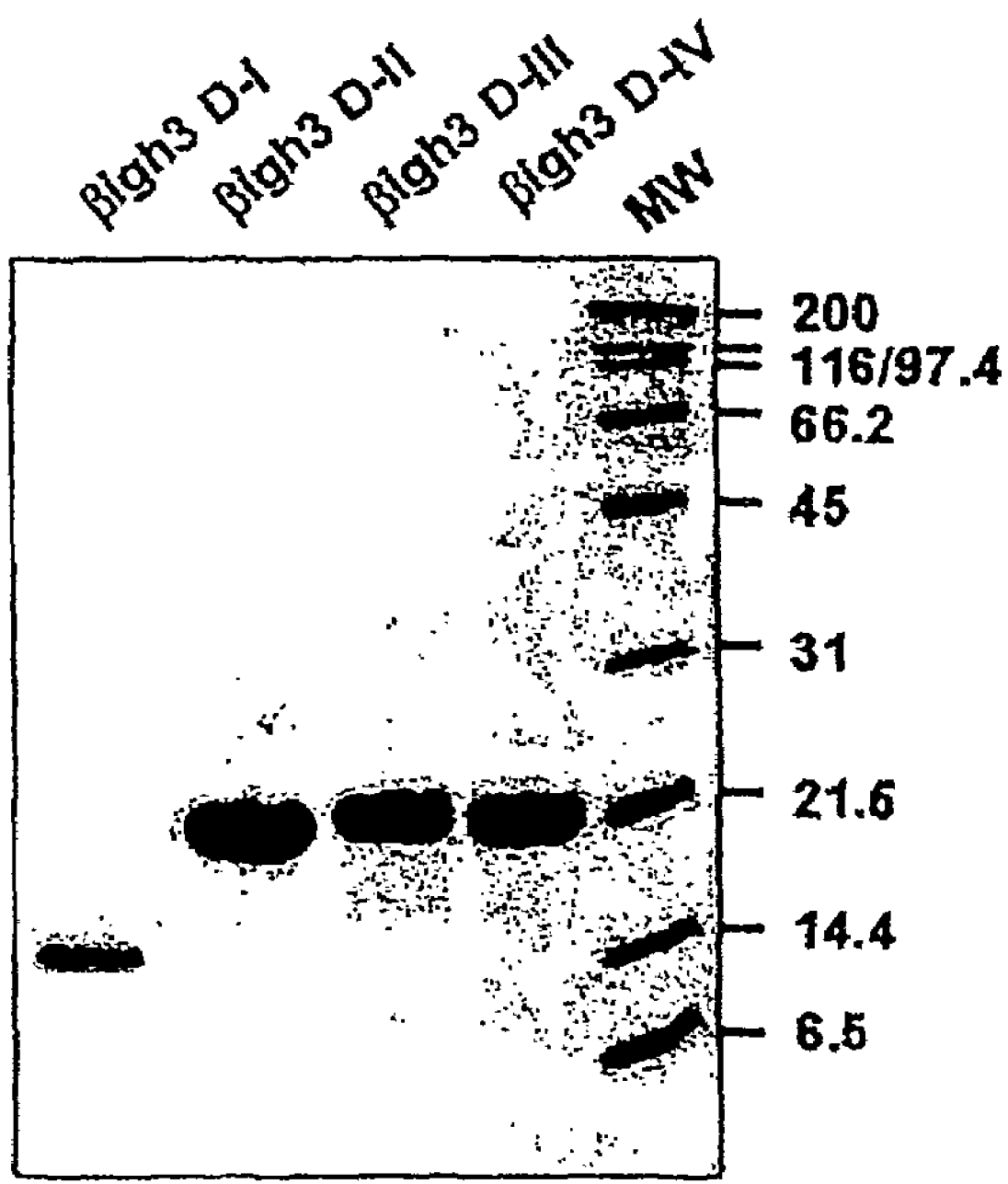
FIG. 8 is a photograph showing SDS-PAGE results of recombinant proteins containing fas-1 domains of βig-h3.

Expression and purification of the recombinant proteins βig-h3 D-1, βig-h3 D-II, βig-h3 D-III, and βig-h3 D-IV followed the procedure described in Example 1-1 and they were identified by SDS-PAGE, as shown in FIG. 8.

Figure 9:
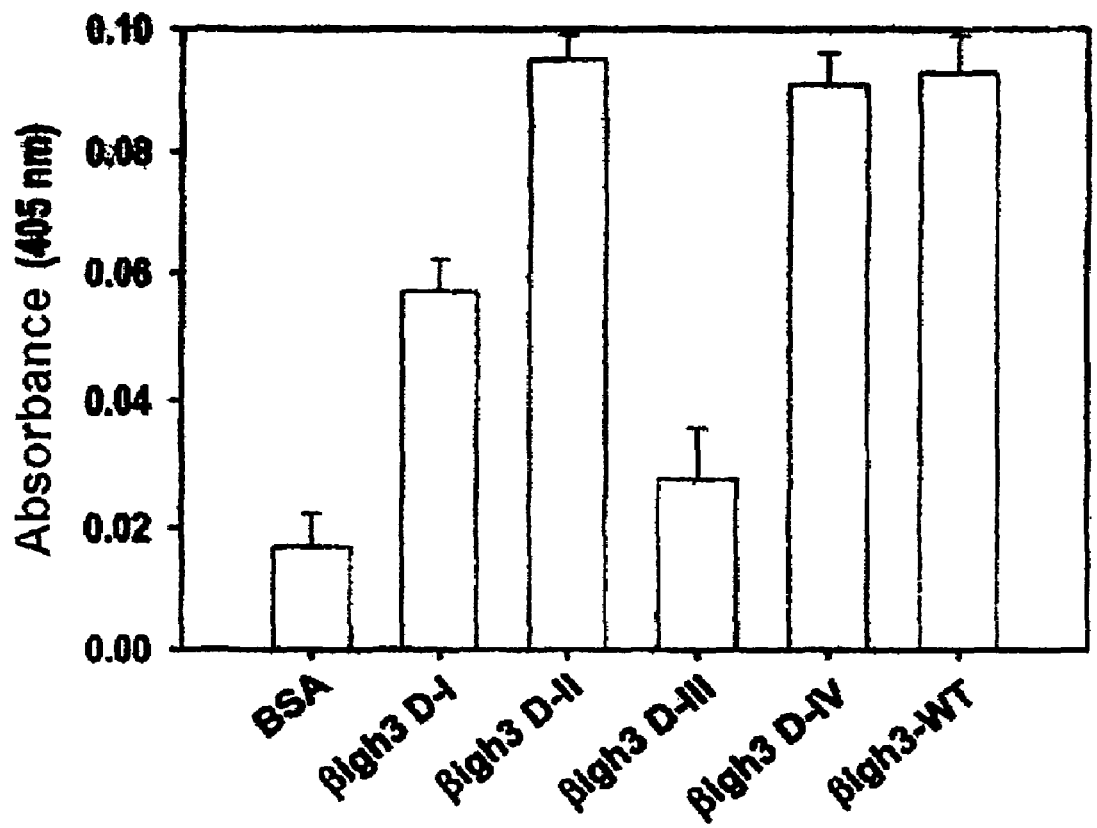
FIG. 9 is a histogram showing HCE cell adhesion activities of recombinant proteins containing fas-1 domains of βig-h3.

In regard to the mediation of cell adhesion, the $2^{nd}$ and $4^{th}$ fas-1 domains were equally active compared to the wild type βig-h3 whereas the $1^{st}$ fas-1 domain was weak and the $3^{rd}$ fas-1 domain was not active at all, as shown in FIG. 9.

Figure 10:
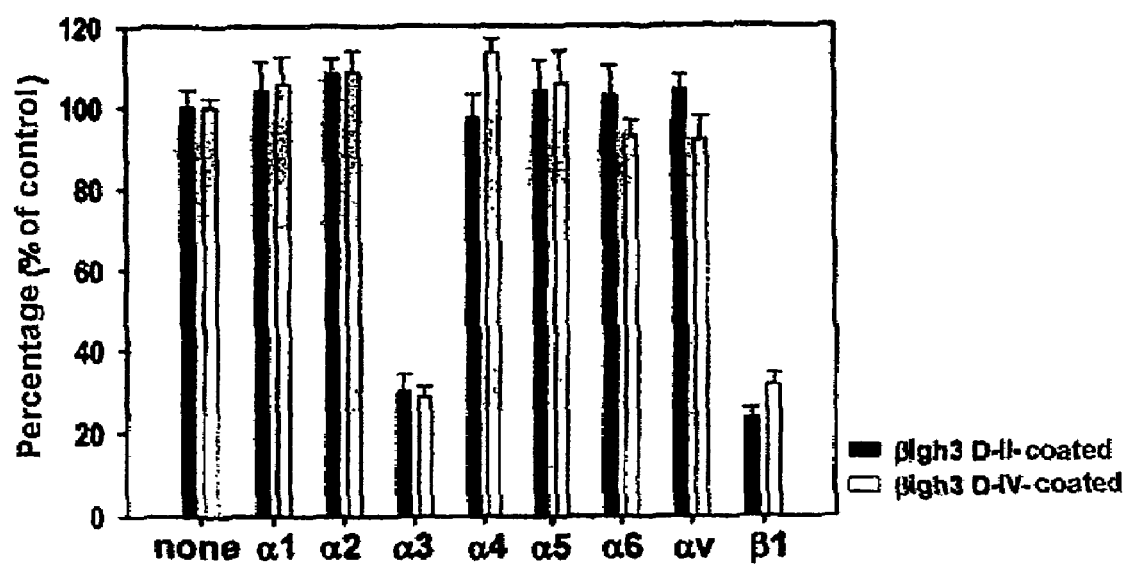
FIG. 10 is a histogram showing the inhibitory effects of anti-integrin antibodies on HCE cell adhesion activities of the recombinant proteins containing fas-1 domains of βig-h3.

In experiments with function-blocking antibodies to integrin subunits, both $2^{nd}$ and $4^{th}$ fas-1 domain-mediated cell adhesion were almost fully blocked by antibodies to α3 and β1 integrins, suggesting that both $2^{nd}$ and $4^{th}$ fas-1 domains have amino acids essential for interacting with α3β1 integrin, as shown in FIG. 10. These results also support the conclusion that neither H1 nor H2 sequence mediates cell adhesion activity of βig-h3 because the $1^{st}$ and $3^{rd}$ domains are not active in cell adhesion, although they have H1 or H2 sequence.

Example 3

Identification of Conserved Amino Acid Sequence Essential for Cell Adhesion of βig-h3

3-1: Identification of Conserved Motif by Amino Acid Sequence Alignment

To find the amino acid sequence responsible for cell adhesion in $2^{nd}$ and $4^{th}$ fas-1 domains of βig-h3, which independently show cell attachment, a computer search based on homologies not only among the repeated fas-1 domains of βig-h3, but also among fas-1 domains of other proteins was carried out. As a result, two amino acids, aspartic acid and isoleucine, near the H2 region, were found to be highly conserved among various proteins, as shown in FIG. 11. In addition, it was found that aspartic acid and isoleucine are both conserved in the $2^{nd}$ and $4^{th}$ fas-1 domains of βig-h3, which are of high cell attachment activity, while only aspartic acid is conserved in the $1^{st}$ fas-1 domain, which shows intermediate cell attachment activity. As for the $3^{rd}$ fas-1 domain which shows no cell attachment activity, it has neither of the two amino acids. This fact is further evidence that the aspartic acid and isoleucine residues near the $H_2$ region are indispensable for mediating the cell attachment and spreading activity.

Figure 12:
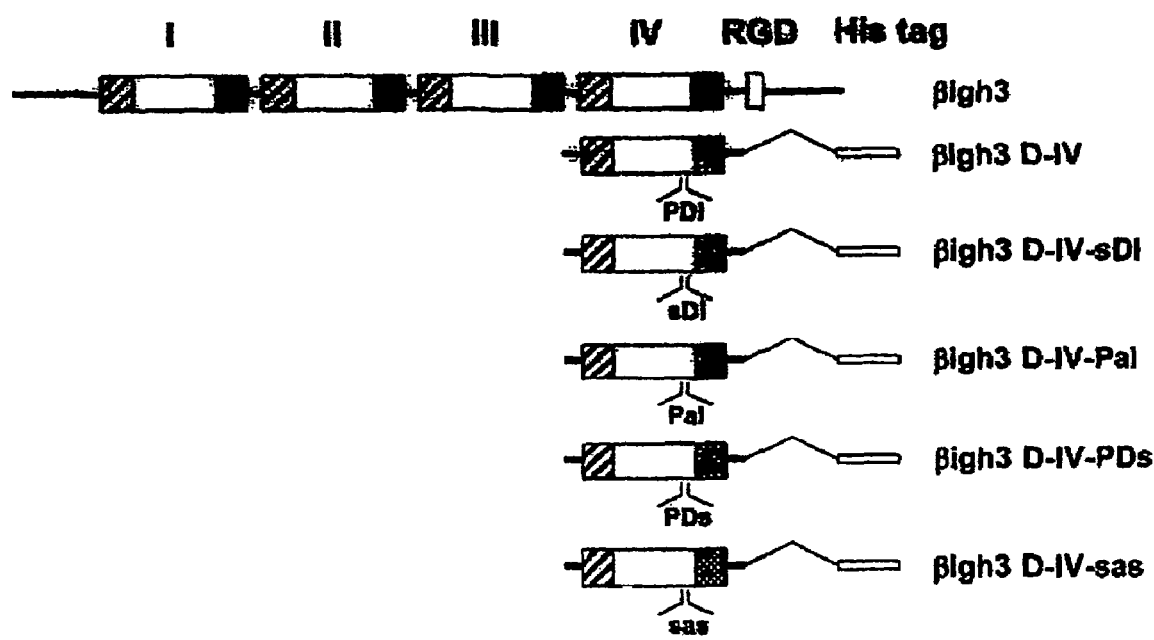
FIG. 12 is a schematic diagram showing substitution mutants of the $4^{th}$ domain of βig-h3.
Figure 13:
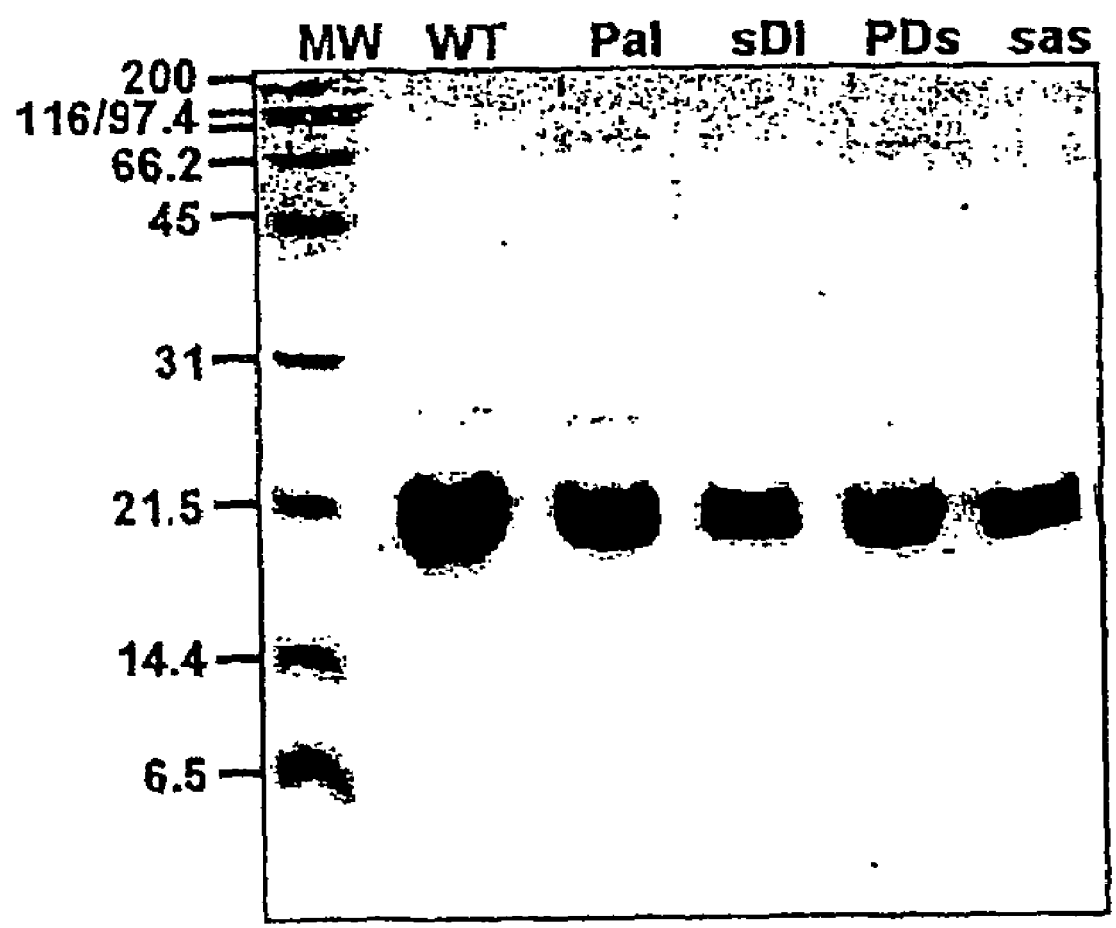
FIG. 13 is a photograph showing SDS-PAGE results of recombinant substitution mutants of the $4^{th}$ domain of βig-h3.

3-2: Identification of Cell Adhesion Activity of the Conversed Amino Acid Sequence Using Substitution Mutants To further confirm that the two amino acids are essential for cell adhesion, the recombinant protein containing the $4^{th}$ fas-1 domain of βig-h3 was mutated by substitution as shown in FIG. 12. The substitution mutant of βig-h3 D-IV was prepared by PCR and its sequence was confirmed by base sequencing. The mutant protein was isolated and purified in the same manner as in Example 1-1 and confirmed on SDS-PAGE, as shown in FIG. 13.

Figure 14:
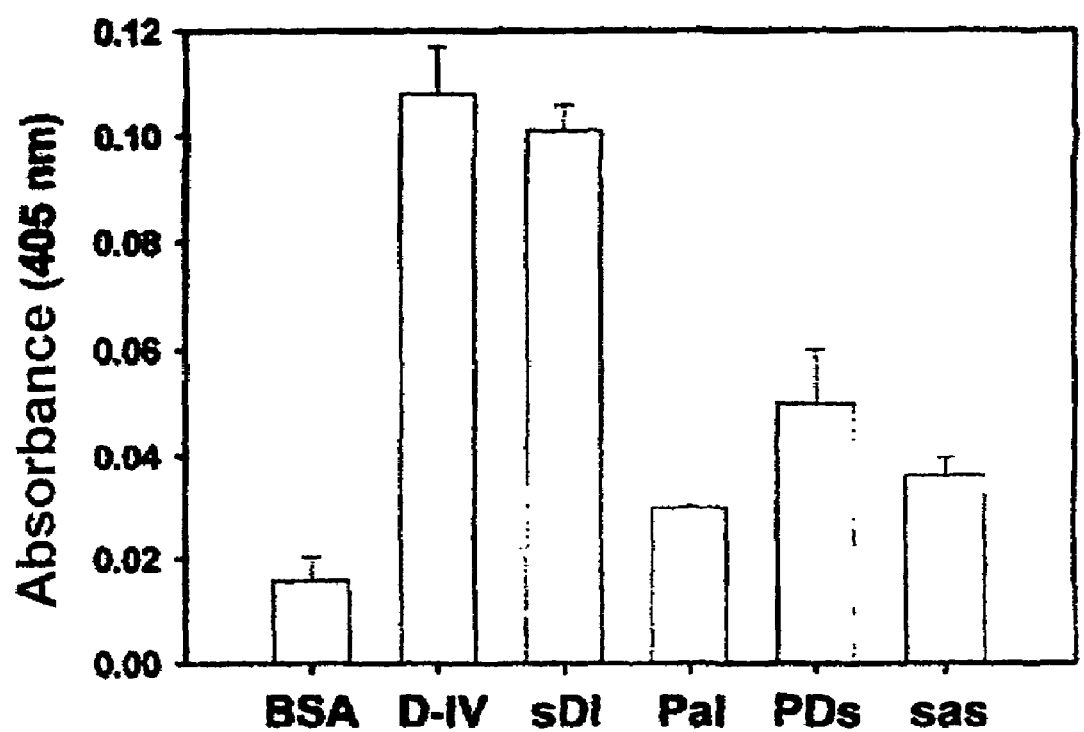
FIG. 14 is a histogram showing cell adhesion activities of substitution mutants of the $4^{th}$ domain of βig-h3.

Examination was made of the cell attachment activity of the mutated proteins wherein the Pro616, Asp617 and Ile618 of βigh3 D-IV were, in combination, substituted with Ser, Ala and Ser, respectively. The mutant protein having Ala instead of Asp617, named D617A (βigh3 D-IV-PaI) and the mutant protein having Ser instead of Ile618, named I618S (βigh3 D-IV-PDs) significantly blocked cell adhesion whereas the mutant protein having Ser instead of Pro616, named P616S (βigh3 D-IV-sDI) was found to have no influence on cell adhesion activity. As for the mutant protein in which the three amino acids were mutated, named P616S/D617A/I618S (βigh3 DIV-sas), it also blocked cell adhesion, as shown in FIG. 14.

The nearly complete loss of the $1^{st}$ fas-1 domain-mediated cell attachment activity in the $1^{st}$ fas-1 domain mutated at Asp617 and Ile618 proved that the aspartic acid at position 617 and isoleucine at position 618 are very important in mediating the cell attachment activity of βigh3.

Example 4

Figure 15:
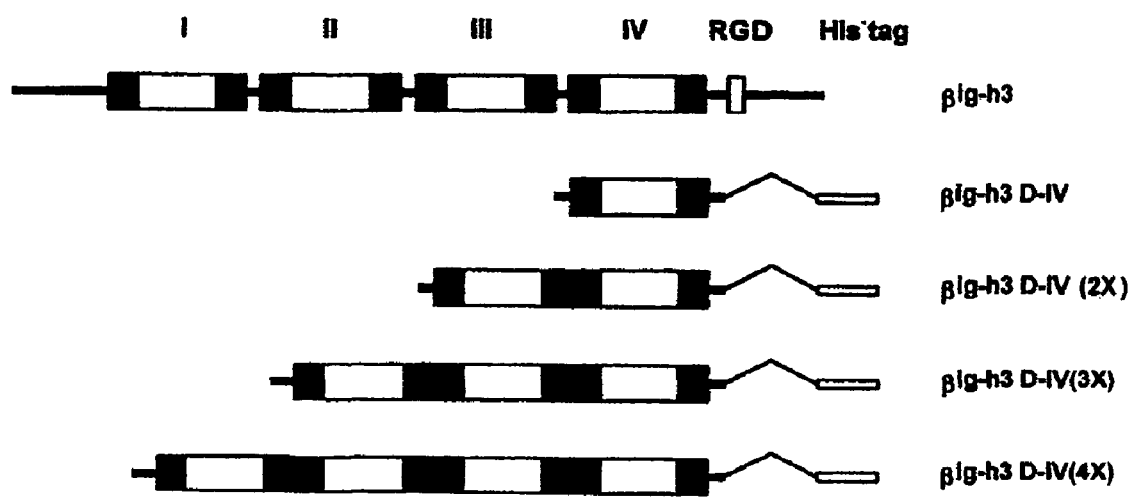
FIG. 15 is a schematic diagram showing recombinant proteins βigh3-D-IV, βigh3-D-IV 2X, 3X and 4X containing one, two, three and four copies of the $4^{th}$ domain of βig-h3.

Identification of βigh3 Domains Effecting Wound Healing 4-1: Expression and Purification of Recombinant βigh3 Protein To examine whether only the βig-h3 domains active in cell adhesion show the same wound healing function as that of the native βig-h3 containing all four fas-1 domains, various recombinant βigh3 proteins were prepared as shown in FIG. 15: His-β-b containing all of 4 fas-1 domains; βigh3-D-IV containing the $4^{th}$ domain alone; and βigh3-D-IV, 2X, 3X and 4X, each containing at least one $4^{th}$ domain. Showing the same cell adhesion activity as in βigh3-WT prepared in Example 1, the recombinant βig-h3 protein His-β-b was prepared from the recombinant expression vector pET-29βanchoring at its EcoRV-EcoRI site an Asp718-BglII fragment which was obtained by deleting a some amino-terminal region from βig-h3 cDNA. The recombinant proteins His-β-b and βigh3-D-IV were expressed and purified in the same manners as in Example 1-1 and 3.

Figure 16:
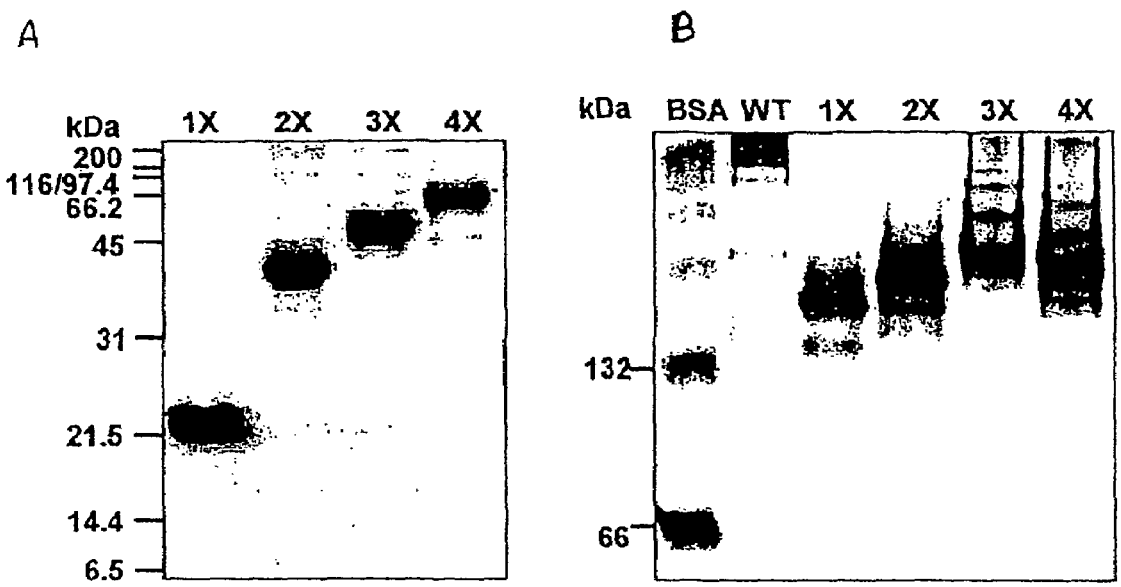
FIG. 16 shows photographs of the recombinant proteins βigh3-D-IV, βigh3-D-IV 2X, 3X and 4X run on 10% SDS-PAGE (A) and 8% nondenaturing PAGE (B), which are purified with the aid of Ni-NTA agarose resin

The recombinant proteins containing at least one $4^{th}$ domain, such as βig3-D-IV, 2X, 3X and 4X were prepared as follows. A DNA fragment encoding to amino acid 498-637 corresponding the $4^{th}$ domain was obtained by PCR and the PCR products were blunt-ended by Klenow enzyme. This blunt-ended cDNA fragment was inserted to the EcoRV site of the pβig-h3 D-IV, which contained the $4^{th}$ domain of βig-h3, and the resulting expression vector was named pβI-h3 D-IV 2X. The insert of the pβig-h3 D-IV 2X was excised by digestion with EcoRV and XhoI and blunt-ended by treatment with Klenow, followed by inserting the blunt-ended fragment into EcoRV sites of pβig-h3 D-IV and pβig-h3 D-IV 2X. The resulting expression vectors were named pβig-h3 D-IV 3X and pβig-h3 D-IV 4X. Expression of all recombinant proteins was induced for 3 hours in the presence of 1 mM IPTG and isolated by use of Ni-NTA resin (Qiagen). Isolated recombinant proteins were purified by elution with 20 mM Tris-HCl comprising 50 mM NaCl and 300 mM imidazole. βig-h3 D-IV 2X, 3X and 4X can be produced in large amounts because they are synthesized as soluble forms, unlike βig-h3 recombinant proteins containing all of the four domains, and do not undergo denaturation, as shown in FIG. 16A. Electrophoresis using non-denaturing gel revealed that βig-h3 D-IV did not form polymers while 2X partially formed polymers and 3X and 4X each readily formed polymers, as shown in FIG. 16B.

*E. coli* BL21/His β-e4X, which harbors the expression vector pβig-h3 D-IV 4X containing four $4^{th}$ domains of βig-h3, was deposited in the Korean Collection for Type Culture of Korea Research Institute of Bioscience and Biotechnology (KRIBB) with accession No. KCTC 0906BP on Dec. 4, 2000.

Fibronectin, serving as a positive control, was purified from citrated rat plasma by affinity chromatography using gelatin-sepharose 4B. The plasma was filtered at room temperature through non-substituted sepharose 4B and the eluate was loaded onto gelatin sepharose 4B equilibrated with 0.05 M Tris-Cl containing 0.05 M EACA (ϵ-amino caproic acid), 0.02 M sodium citrate and 0.02% sodium azide. After being eluted, most plasma proteins were washed with a buffer containing 1 M sodium chloride. Then, absorbed fibronectin was eluted with 3M uric acid isotonic buffer which was subsequently dialyzed for about 48 hours against PBS, pH 7.2, to purify fibronectin. Its concentration was determined by UV absorbance at 280 nm and freeze-dried before being stored at −20° C.

4-2: Assay for Wound Healing Activity of βig-h3 D-IV Containing the 4$^{th}$ Domain To compare wound healing activity between the recombinant βig-h3 protein His-β-b, which contains all of the four fas-1 domains, like native βig-h3 protein, and the recombinant βig-h3 protein βigh3-D-IV, which contains the 4$^{th}$ domain alone, ointment bases comprising the recombinant proteins were tested as follows.

Four dermal whole layer wounds, each 2 cm in diameter, were made on the backs of rats and divided into test groups 1-A, 1-B, 1-C and 1-D according to the ointment applied thereto.

1-A: coated at a dose of 1 gm per day with an ointment base combined with no materials.

1-B: coated at a dose of 1 gm per day with an ointment in which fibronectin was combined at a concentration of 100 μg/ml with a base.

1-C: coated at a dose of 1 g per day with an ointment in which Hisβ-b protein was combined at a concentration of 100 μg/ml with a base.

1-D: coated at a dose of 1 g per day with an ointment in which βigh3-D-IV protein was combined at a concentration of 100 μg/ml with a base.

The backs of etherized rats were shaved, followed by sterilizing the shaved region with betadin solution. In test group 1, the back of each rat was cut by use of a No. 15 surgical blade to form four circular wounds with a diameter of 2 cm penetrating the whole dermal layers. Ointments for test groups 1-A, 1-B, 1-C and 1-D were applied at an amount of about 1 g to the wounds which were then covered with a synthetic dressing (Tegaderm® 3M) and lightly bandaged. Application of ointments was performed once every day.

With a base of an aqueous material (SamA base), each of the ointments contained, per 1 g, spermaceti 38 mg, stearyl alcohol 116 mg, polyethylglycol 38 mg, conc. glycerin 192 mg, ethanol 23 mg, lauryl sodium sulfate mg, ethyl paraoxybenzoate 0.87 mg, butyl paraoxybenzoate 0.12 mg, and purified water.

First, morphologies of wounds were observed. The same scale was positioned near each wound and pictures were taken at the same distance from each wound. Pictures were scanned in a computer and used to measure areas of the wounds with the aid of NIH image analysis system (Bio-Optics). To take the pictures, the muscle was completely relaxed by etherizing the rats. Measurements were performed once every other day until the 22$^{nd}$ day. For comparing test groups, the measured values were analyzed according to ANOVA test and Scheffer's test.

Figure 17:
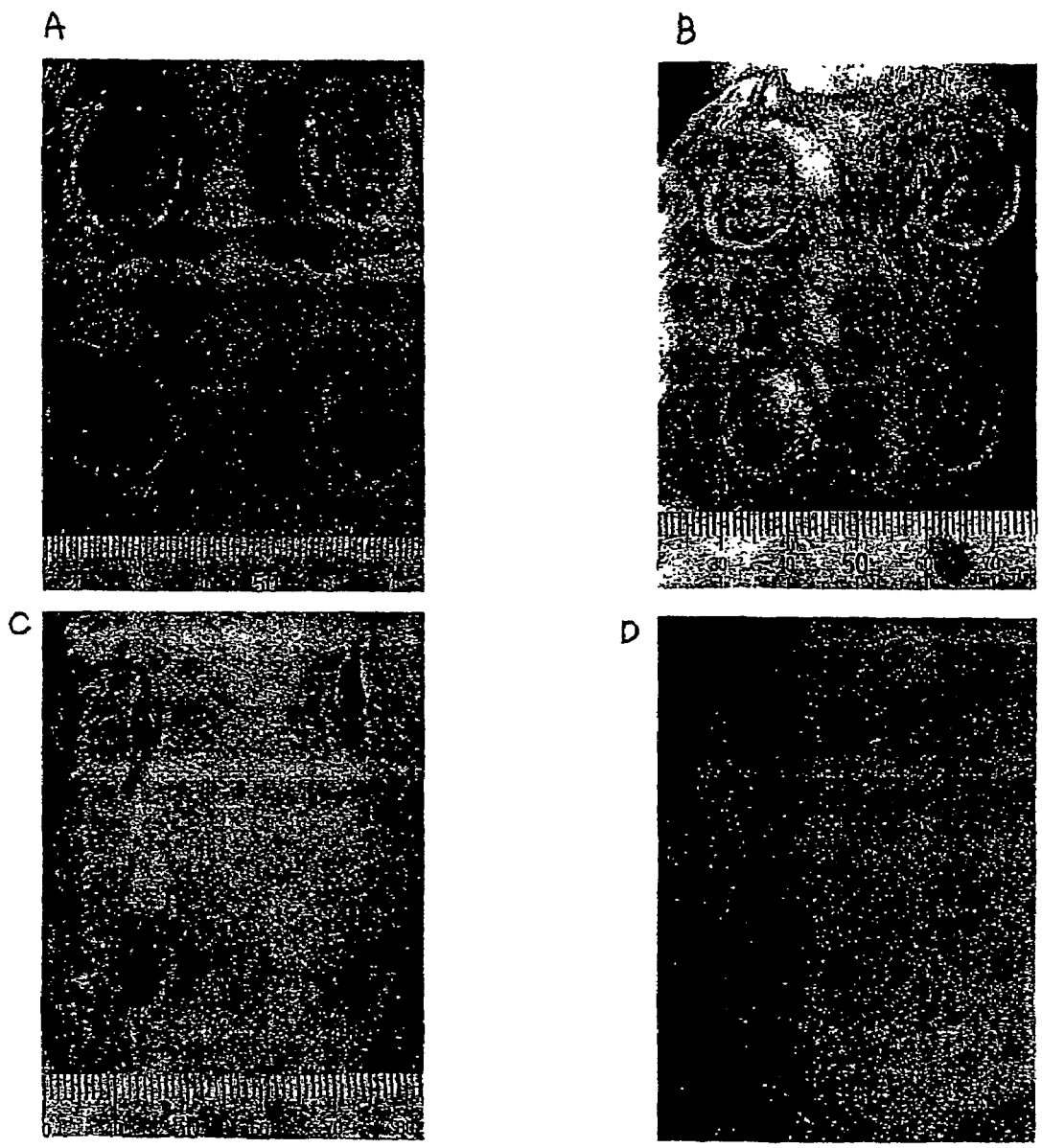
FIG. 17 shows optical photographs of wounds to which an ointment base is applied alone (A) and in combination with fibronectin (B), His-β-b (C), and βig-h3-D-IV (D).

In all test groups, wound areas were observed to be gradually reduced just after the formation of wounds. The test groups to which fibronectin and the recombinant βig-h3 protein were applied were measured to be more quickly reduced in wound area than the test group to which the ointment base alone was applied. A significant difference in wound area was seen after 7 days of ointment application. Statistically, there were significant differences (p<0.05) between wounds of group I-A and the other groups, which did not show a significant difference therebetween. The results are given in Table 1, below and FIG. 17.

TABLE 1

Healing Effect of Ointment Bases Combined with Recombinant βig-h3 Proteins on Wounds

| Group | Day | | | | | | | | | | | |
|---|---|---|---|---|---|---|---|---|---|---|---|---|
| | 0 | 2* | 4 | 6 | 8* | 10* | 12 | 14 | 16 | 18 | 20 | 22 |
| I-A (Control) | 3.15 ± 0.49 | 3.09$^a$ ± 0.31 | 2.45 ± 0.39 | 2.17 ± 0.46 | 1.64$^a$ ± 0.50 | 1.80$^a$ ± 0.11 | 0.84 ± 0.32 | 0.56 ± 0.31 | 0.34 ± 0.07 | 0.19 ± 0.04 | 0.17 ± 0.05 | 0.08 ± 0.01 |
| I-B (Fibronectin) | 3.17 ± 0.78 | 2.38$^b$ ± 0.55 | 2.01 ± 0.54 | 1.83 ± 0.42 | 1.39$^b$ ± 0.38 | 1.26$^b$ ± 0.18 | 0.54 ± 0.11 | 0.39 ± 0.12 | 0.25 ± 0.12 | 0.16 ± 0.09 | 0.12 ± 0.09 | 0.06 ± 0.03 |
| I-C (His-β-b) | 3.14 ± 0.46 | 2.58$^b$ ± 0.47 | 1.89 ± 0.26 | 1.71 ± 0.33 | 1.42$^b$ ± 0.45 | 1.37$^b$ ± 0.71 | 0.46 ± 0.06 | 0.36 ± 0.13 | 0.26 ± 0.09 | 0.15 ± 0.10 | 0.11 ± 0.03 | 0.03 ± 0.01 |
| I-D (βig-h3-D-IV) | 3.15 ± 0.43 | 2.62$^b$ ± 0.52 | 2.37 ± 0.45 | 1.98 ± 0.52 | 1.51$^b$ ± 0.21 | 0.98$^b$ ± 0.69 | 0.44 ± 0.24 | 0.22 ± 0.09 | 0.20 ± 0.09 | 0.18 ± 0.10 | 0.13 ± 0.07 | 0.06 ± 0.01 |

Value: mean ± SD
*p < 0.05 by ANOVA and Scheffe's test
$^{a, b}$vertically significant difference of data in statistics Histological analysis was conducted under an optical microscope. Biopsies of wound sites were taken at days 3, 7, 10, 14 and 20, and fixed in 10% formalin and solidified with paraffin. 6 μm slices of the samples were dyed with hematoxylin-eosin (H&E) and Masson's trichrome before observation under a microscope. Wound healing effects according to time of each test material were evaluated through re-epithelialization and formation of collagenous fibers. In the case of re-epithelialization, epithelial formation was semi-quantified in such a way that zero was set for the formation of no epithelial layers, 1+ for initiation of epithelialization, 2+ for incomplete epithelial layer structure, and 3+ for complete epithelial layer structure. Regarding comparison among test groups and differences according to time within each group, measured values were statistically analyzed using ANOVA test and Scheffe's test. As for collagenous fiber formation, it was graded as 1+ for insignificant formation of collagenous fibers as observed with trichrome dye, 2+ for scatteringly spaced collagenous fibers, and 3+ for dense collagenous fibers.

Figure 18:
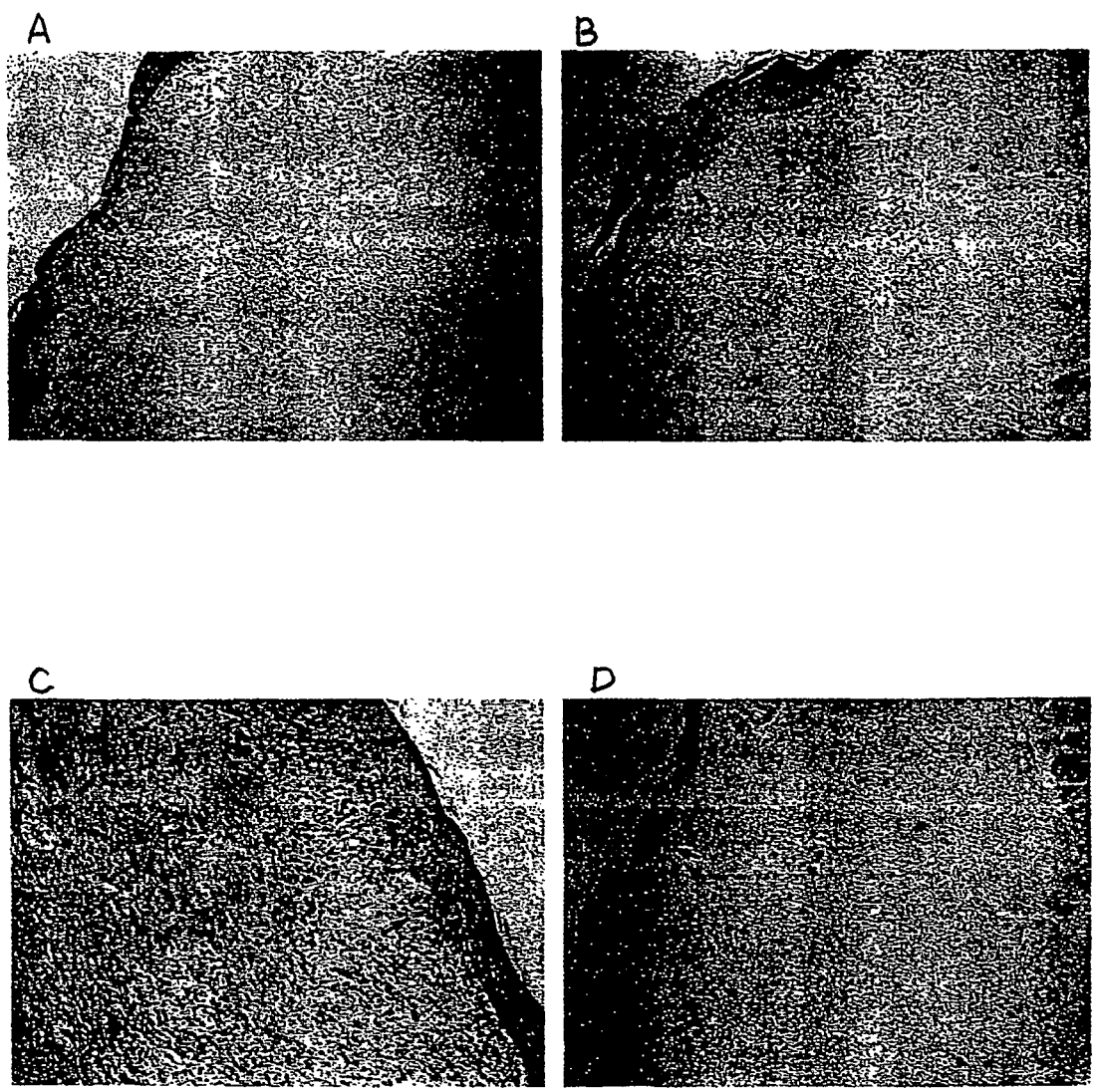
FIG. 18 shows microphotographs of wounds which are in the process of re-epithelialization after being treated with an ointment base alone (A) and in combination with fibronectin (B), His-β-b (C), and βig-h3-D-IV (D).

As observed by an optical microscope, re-epithelialization appeared to start at day 7 to 10 in test groups 1-B, 1-C and 1-D and be completed at day 20. In the case of the control group 1-A, on the other hand, re-epithelialization was not yet initiated even at day 14 and was not completed at day 20. The results are given in Table 2, below and FIG. 18.

TABLE 2

Re-ephithelialization of Wound

| Group | Day | | | | |
|---|---|---|---|---|---|
| | 3 | 7 | 10 | 14 | 20 |
| 1-A (Control) | 0 | 0 | 0 | 0 | 2+ |
| 1-B Fibronectin) | 0 | 1+ | 1+ | 2+ | 3+ |
| 1-C (His-β-b) | 0 | 0 | 1+ | 2+ | 3+ |
| 1-D (βigD-IV) | 0 | 0 | 1+ | 2+ | 3+ |

Figure 19:
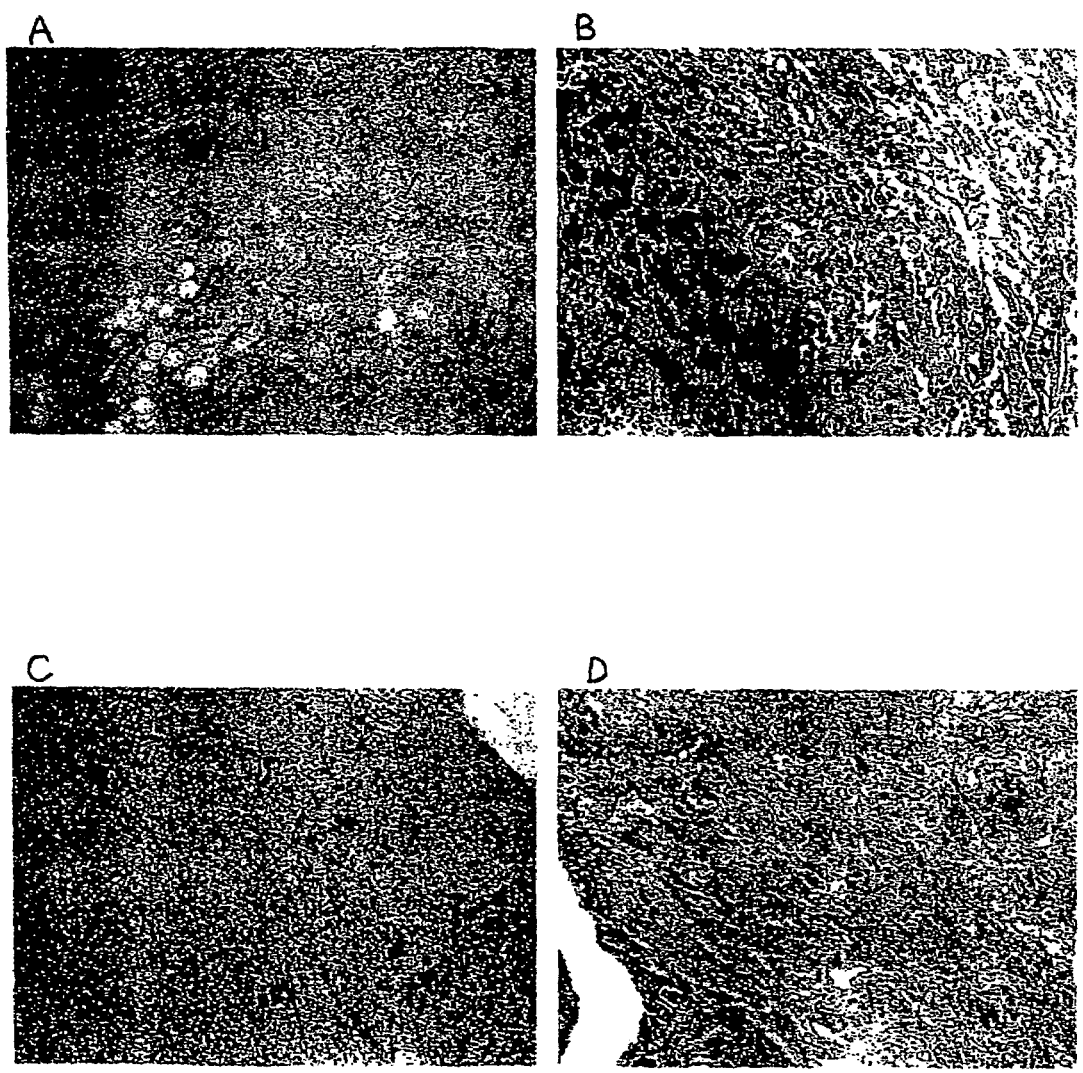
FIG. 19 shows optical photographs of wounds which have collagenous fibers formed after being treated with an ointment alone (A) and in combination with fibronectin (B), His-β-b (C), and βig-h3-D-IV (D).

Results for formation of collagenous fibers are given in Table 3, below. As seen in Table 3, collagenous fibers were not significantly formed in test groups 1-A and 1-D until day 7 with maintenance of grade +1, whereas test groups 1-B and 1-C were graded as 2+. However, all test groups were graded as 2+ at day 10 with relatively rich collagenous fibers. At day 14, it was observed that collagenous fibers were densely formed and well arranged with grade +3, as shown in FIG. 19. Naturally, denser collagenous fibers reflect more improved wound healing progress.

TABLE 3

Formation Behavior of Collagenous Fibers at Wound

| Group | Day | | | | |
|---|---|---|---|---|---|
| | 3 | 7 | 10 | 14 | 20 |
| 1-A (Control) | 1+ | 1+ | 2+ | 3+ | 3+ |
| 1-B (Fibronectin) | 1+ | 2+ | 2+ | 3+ | 3+ |
| 1-C (His-β-b) | 1+ | 2+ | 2+ | 3+ | 3+ |
| 1-D (βigD-IV) | 1+ | 1+ | 2+ | 3+ | 3+ |

Formation grade of collagenous fibers
0: negative,
1+: insignificant,
2+: scatteringly formed,
3+: very dense 4-3: Wound Healing Effect of at Least One $4^{th}$ Domain-Containing Recombinant Proteins βigh3-D-IV, βig-h3 D-IV 2X, 3X and 4X Based on the finding that βigh3-D-IV containing only the $4^{th}$ domain is efficient for wound healing, βigh3-D-IV 2X, 3X and 4X, which contained the $4^{th}$ domain in duplicate, triplicate and quadruplicate, respectively, were prepared in order to assay for wound healing activity.

Figure 20:
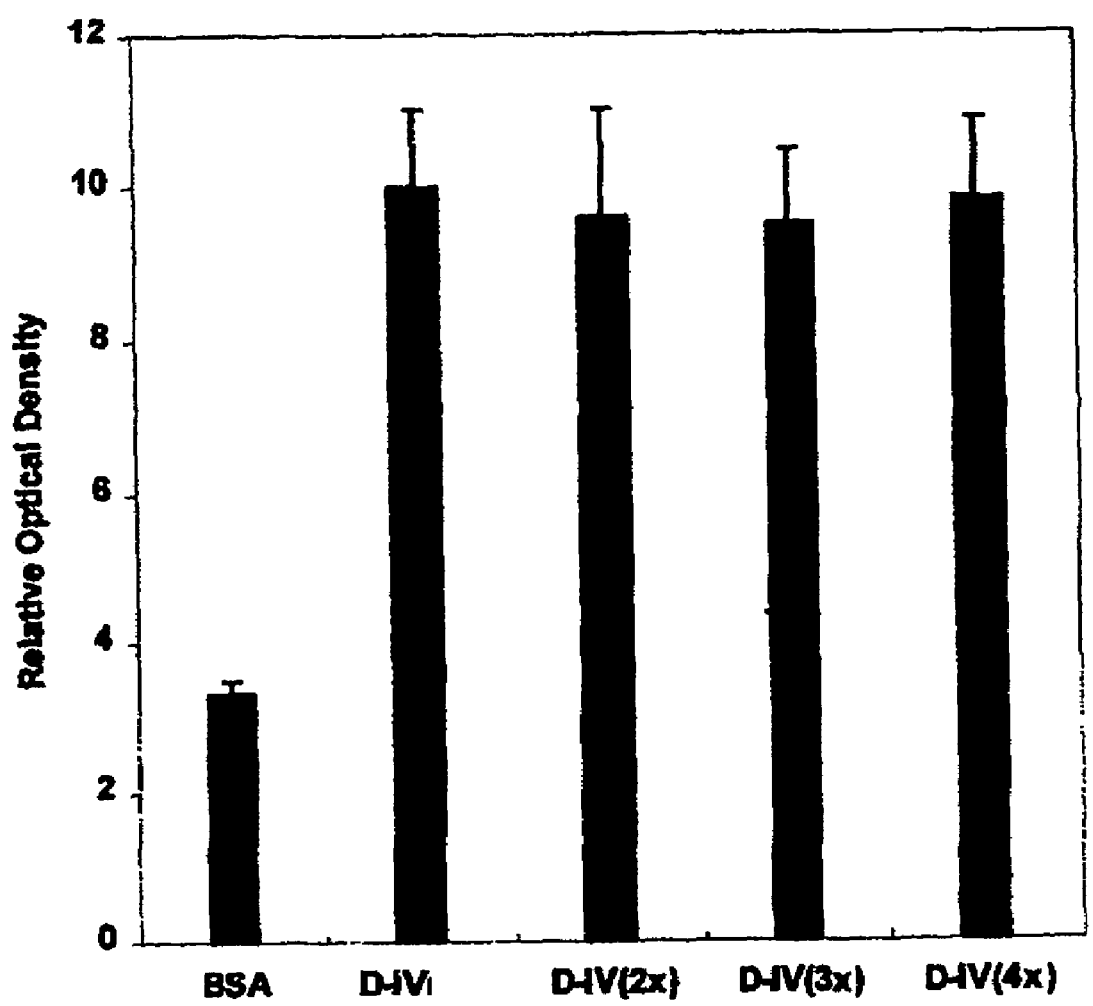
FIG. 20 is a histogram showing HCE cell adhesion activities of the recombinant proteins βigh3-D-IV, βigh3-D-IV 2X, 3X and 4X, which contain at least one copy of the $4^{th}$ domain of βig-h3.

The recombinant proteins were assayed for HCE cell adhesion activity in the same manner as in Example 1-2. The results are given in FIG. 20. As seen, the recombinant proteins βig-h3 D-IV 2X, 3X and 4X were all found to effectively induce the adhesion of HCE cells.

In order to examine wound healing effects of the recombinant proteins, the following experiments were conducted.

Adult Spraque-Dawley lineage rats with a body weight of 250-300 gm were raised with standard feedstuff at a constant temperature and humidity.

In test group 2, four circular dermal whole layer wounds were made on the back of each rat and coated with chitosan bases combined with materials of interest:

2-A: wound coated with chitosan base only
2-B: wound coated with chitosan base in combination with 500 μg/ml of fibronectin
2-E: wound coated with chitosan base in combination with 500 μg/ml of βig-h3 D-IV 3X protein
2-F: wound coated with chitosan base in combination with 500 μg/ml of βig-h3 D-IV 4X protein The composites based on chitosan were prepared as follows. 1 g of water soluble chitosan (poly(1-4) 2-amino-2-deoxy-β-D-glucan) with a molecular weight of 600,000 Da was dissolved in 100 ml of sterile distilled water and the resulting 1% solution was dispensed in aliquot of 2 ml to to 12-well plate (Corning, USA), followed by the addition of 100 μg of gentamycin per well. Fibronectin, βigh3-D-IV 3X, and βigh3-D-IV 4X were individually added to a concentration of 500 μg/ml and frozen at −70° C., followed by freeze-drying in a freeze drier (Ilshin) for 12 hours to give disc-shaped composites.

The backs of etherized rats were shaved, followed by sterilizing the shaved region with betadin solution. Penetrating the whole dermal layers, four circular wounds with a diameter of 7 mm were formed on the back of each rat. The wounds were covered with composites used for test groups 2-A, 2-B, 2-E and 2-F, respectively, and then with Tegaderm® (3M) and lightly bandaged. The composites were changed with fresh ones every three days.

Wound healing effects were evaluated by determining appearances of the wounds as in Example 4-2.

A high wound healing effect was obtained from the composite containing the recombinant protein βig-h3 D-IV 3X or 4X.

All rats, except for all members in the test group 2-A, one in the test group 2-B and two in test groups 2-E and 2-F each, were completely recovered from the wound at day 12 to 15. All wound areas reduced in size just after the formation of wound. As for the test group 2-A, its wound area was observed to be reduced at a relatively slow rate throughout the period of healing time. In the other test groups, the wound areas were reduced greatly in the first three days, gradually to day 9, and then greatly again. Turning to comparison among wounds, there were more significant differences (p<0.05) for the whole period of 15 days in the test groups 2-B, 2-E and 2-F, than in the test group 2-A, as shown in Table 4 and FIG. 21.

TABLE 4

Reduction of Wound Area (mm$^2$)

| Group | Day | | | | | |
|---|---|---|---|---|---|---|
| | 0 | 3* | 6* | 9* | 12* | 15* |
| 2-A (Chitosan) | 49.3 ± 4.0 | 34.5 ± 0.6$^a$ | 26.1 ± 0.5$^a$ | 13.8 ± 0.5$^a$ | 10.8 ± 0.3$^a$ | 3.4 ± 0.2$^a$ |
| 2-B (Chitosan + Fibronectin) | 49.2 ± 0.5 | 24.1 ± 0.6$^b$ | 12.9 ± 0.6$^b$ | 9.7 ± 0.8$^b$ | 3.2 ± 0.4$^b$ | 0.8 ± 0.2$^b$ |
| 2-C | 49.2 ± 1.5 | 25.3 ± 0.7$^b$ | 16.6 ± 0.6$^b$ | 11.2 ± 0.5$^b$ | 5.0 ± 0.8$^b$ | 1.2 ± 0.2$^b$ |

TABLE 4-continued

| | Reduction of Wound Area (mm²) | | | | | |
|---|---|---|---|---|---|---|
| | Day | | | | | |
| Group | 0 | 3* | 6* | 9* | 12* | 15* |
| (Chitosan + βig-h3 3×) 2-D (Chitosan + βig-h3 4×) | 48.5 ± 0.4 | 24.5 ± 0.6[b] | 14.1 ± 0.7[b] | 9.6 ± 0.6[b] | 4.2 ± 0.3[b] | 1.1 ± 0.2[b] |

Value: Mean ± S.D
*p < 0.05 by ANOVA test
[a, b] significant difference of data in statistics Consequently, the recombinant proteins of the present invention, which contain the $2^{nd}$ and $4^{th}$ domains of βig-h3, alone or incombination, or in multiplicate are effective for cell adhesion and wound healing and ultimately can be utilized in developing cell culture and wound healing agents.

INDUSTRIAL APPLICABILITY

In the present invention, there are provided recombinant proteins containing at least one of the $2^{nd}$ and $4^{th}$ domains of βig-h3 in which one aspartic acid and one isoleucine residue, known to be essential for association with integrin, are highly conserved. Also, the recombinant proteins themselves are useful for cell adhesion and wound healing, making a contribution to the development of cell culture methods and wound healing agents.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for inducing cell adhesion comprising coating a recombinant protein comprising one or more copies of the $4^{th}$ fas-1 domain of βig-h3 onto a support and binding mammalian cells to the protein-coated support, wherein the recombinant protein does not include full-length βig-h3 protein.

2. The method according to claim 1, wherein the $4^{th}$ fas-1 domain of βig-h3 consists of the amino acid sequence 498-637 of human βig-h3 (SEQ ID NO: 26).

3. The method according to claim 1, wherein the recombinant protein comprises the amino acid sequence 502-637 of human βig-h3 (SEQ ID NO: 27) in quadruplicate.

4. The method according to claim 1, wherein the recombinant protein further comprises one or more copies of the $2^{nd}$ fas-1 domain of βig-h3.

5. The method according to claim 4, wherein the $2^{nd}$ fas-1 domain of βig-h3 consists of the amino acid sequence 237-377 of human βig-h3 (SEQ ID NO: 24).

6. The method according to claim 4, wherein the $4^{th}$ fas-1 domain of βig-h3 consists of the amino acid sequence 498-637 of human βig-h3 (SEQ ID NO: 26).

7. The method according to claim 4, wherein the recombinant protein comprises the amino acid sequence 502-637 of human βig-h3 (SEQ ID NO: 27) in quadruplicate.

8. A method for inducing cell adhesion comprising coating a recombinant protein comprising two or more copies of the $2^{nd}$ and/or the $4^{th}$ fas-1 domain of βig-h3 onto a support and binding mammalian cells to the protein-coated support.

9. The method according to claim 8, wherein the $2^{nd}$ fast-1 domain of βig-h3 consists of the amino acid sequence 237-377 of βig-h3 (SEQ ID NO: 24).

10. The method according to claim 8, wherein the $4^{th}$ fas-1 domain of βig-h3 consists of the amino acid sequence 498-637 of βig-h3 (SEQ ID NO: 26).

11. A method according to claim 8, wherein the recombinant protein comprises the amino acid sequence 502-637 of βig-h3 in quadruplicate (SEQ ID NO: 27).

12. A method for inducing cell adhesion comprising coating a recombinant protein consisting of one or more copies of the $2^{nd}$ and/or the $4^{th}$ fas-1 domain of βig-h3, alone or in combination, onto a support and binding mammalian cells to the protein-coated support.

13. The method according to claim 12, wherein the $2^{nd}$ fas-1 domain of βig-h3 consists of the amino acid sequence 237-377 of βig-h3 (SEQ ID NO: 24).

14. The method according to claim 12, wherein the $4^{th}$ fas-1 domain of βig-h3 consists of the amino acid sequence 498-637 of βig-h3 (SEQ ID NO: 26).

15. The method according to claim 12, wherein the recombinant protein consists of the amino acid sequence 502-637 of βig-h3 (SEQ ID NO: 27) in quadruplicate.

16. A method for inducing cell adhesion comprising the steps of:
   1) preparing a recombinant protein comprising one or more copies of the $4^{th}$ fas-1 domain of βig-h3, by use of an expression vector, wherein the recombinant protein does not include full-length βig-h3 protein;
   2) coating the recombinant protein onto a solid support; and
   3) binding mammalian cells to the protein-coated solid support.

17. A method for healing a mammalian wound with a recombinant protein comprising one or more copies of the $2^{nd}$ and/or the $4^{th}$ fas-1 domain of βig-h3, wherein the recombinant protein does not include full-length βig-h3 protein, comprising the steps of:
   1) coating a solid support with the recombinant protein comprising one or more copies of the $2^{nd}$ and/or the $4^{th}$ fas-1 domain of βig-h3;
   2) binding mammalian cells to the protein-coated solid support; and
   3) attaching said solid support to the wound.

* * * * *